(12) United States Patent
Salvermoser et al.

(10) Patent No.: US 11,931,269 B2
(45) Date of Patent: Mar. 19, 2024

(54) DELIVERY SYSTEMS FOR INTERSPINOUS, INTERLAMINAR STABILIZATION DEVICES AND METHODS OF USE

(71) Applicant: Xtant Medical, Inc., Belgrade, MT (US)

(72) Inventors: Markus Salvermoser, Tuttlingen-Möhringen (DE); Stephan Eckhof, Rietheim-Weilheim (DE)

(73) Assignee: XTANT MEDICAL, INC., Belgrade, MT (US)

( * ) Notice: Subject to any disclaimer, the term of this patent is extended or adjusted under 35 U.S.C. 154(b) by 350 days.

(21) Appl. No.: 16/031,455

(22) Filed: Jul. 10, 2018

(65) Prior Publication Data
US 2019/0008656 A1     Jan. 10, 2019

Related U.S. Application Data

(60) Provisional application No. 62/530,561, filed on Jul. 10, 2017.

(51) Int. Cl.
*A61F 2/46*     (2006.01)
*A61F 2/44*     (2006.01)

(52) U.S. Cl.
CPC ............ *A61F 2/4611* (2013.01); *A61F 2/44* (2013.01); *A61F 2/4684* (2013.01); *A61F 2/4603* (2013.01); *A61F 2002/4622* (2013.01); *A61F 2002/4627* (2013.01); *A61F 2002/4635* (2013.01); *A61F 2002/4687* (2013.01)

(58) Field of Classification Search
CPC ............ A61F 2/4611; A61F 2002/4615; A61F 2002/4635; A61F 2002/4627; A61B 17/7062; A61B 17/7071; A61B 17/7067; A61B 17/3468
See application file for complete search history.

(56) References Cited

U.S. PATENT DOCUMENTS

| | | | | |
|---|---|---|---|---|
| 5,645,599 A * | 7/1997 | Samani | ............... | A61B 17/7062 623/17.16 |
| 6,068,630 A * | 5/2000 | Zucherman | .......... | A61B 17/025 606/249 |
| 6,723,126 B1 * | 4/2004 | Berry | ..................... | A61F 2/4611 606/247 |
| 7,585,316 B2 * | 9/2009 | Trieu | .................. | A61B 17/7065 606/249 |
| 7,955,392 B2 * | 6/2011 | Dewey | ............... | A61B 17/7068 623/17.16 |
| 7,985,246 B2 * | 7/2011 | Trieu | .................. | A61B 17/7065 606/279 |
| 8,303,630 B2 * | 11/2012 | Abdou | ............... | A61B 17/7067 606/249 |
| 8,388,656 B2 * | 3/2013 | Sheffer | ............. | A61B 17/7065 606/248 |

(Continued)

*Primary Examiner* — David W Bates
(74) *Attorney, Agent, or Firm* — Sheridan Ross P.C.

(57) ABSTRACT

The present disclosure provides various surgical instruments and delivery systems to properly implant spinous stabilization devices, such as for example, interspinous, interlaminar stabilization devices, in a less invasive manner than what is currently performed. The delivery system may be a tubular delivery system through which instruments and devices can pass. Methods for using these surgical instruments and delivery systems are also provided.

19 Claims, 31 Drawing Sheets

(56) References Cited

U.S. PATENT DOCUMENTS

| | | | | |
|---|---|---|---|---|
| 8,470,000 B2* | 6/2013 | Trautwein | ........... | A61B 17/7049 606/249 |
| 8,491,598 B2* | 7/2013 | Crook | ................... | A61F 2/4611 606/99 |
| 8,968,365 B2* | 3/2015 | Aschmann | ......... | A61B 17/7053 606/248 |
| 8,986,307 B2* | 3/2015 | Kirschman | ............ | A61F 2/4465 606/86 A |
| 9,173,686 B2* | 11/2015 | Sheffer | .............. | A61B 17/7062 |
| 9,381,047 B2* | 7/2016 | Sheffer | .............. | A61B 17/7062 |
| 9,668,783 B2* | 6/2017 | Goel | ................ | A61B 17/1757 |
| 9,987,053 B2* | 6/2018 | Milz | .................. | A61B 17/7076 |
| 10,758,361 B2* | 9/2020 | Blain | ................. | A61F 2/4405 |
| 10,835,295 B2* | 11/2020 | Altarac | ............... | A61B 17/7067 |
| 11,006,982 B2* | 5/2021 | Abdou | ................ | A61B 17/7067 |
| 11,179,248 B2* | 11/2021 | Abdou | .................. | A61F 2/4455 |
| 2002/0045904 A1* | 4/2002 | Fuss | ...................... | A61F 2/4611 606/99 |
| 2003/0208203 A1* | 11/2003 | Lim | ...................... | A61B 17/808 606/86 A |
| 2004/0117019 A1* | 6/2004 | Trieu | ....................... | A61F 2/441 623/17.11 |
| 2004/0153065 A1* | 8/2004 | Lim | ...................... | A61F 2/4611 606/53 |
| 2005/0049705 A1* | 3/2005 | Hale | .................. | A61B 17/1671 623/17.11 |
| 2005/0240193 A1* | 10/2005 | Layne | ................ | A61B 17/1671 606/80 |
| 2006/0036258 A1* | 2/2006 | Zucherman | .......... | A61B 17/025 606/90 |
| 2006/0229627 A1* | 10/2006 | Hunt | .................... | A61F 2/4465 606/86 R |
| 2007/0093828 A1* | 4/2007 | Abdou | ............... | A61B 17/7077 606/86 A |
| 2007/0135814 A1* | 6/2007 | Farris | ................. | A61B 17/7064 606/279 |
| 2007/0142843 A1* | 6/2007 | Dye | ..................... | A61F 2/4611 606/99 |
| 2007/0185490 A1* | 8/2007 | Implicito | ............. | A61B 17/025 606/249 |
| 2007/0233076 A1* | 10/2007 | Trieu | .................. | A61B 17/7065 606/249 |
| 2007/0233245 A1* | 10/2007 | Trieu | .................... | A61F 2/4611 623/17.11 |
| 2008/0015609 A1* | 1/2008 | Trautwein | .......... | A61B 17/7062 606/99 |
| 2008/0114371 A1* | 5/2008 | Kluger | .................. | A61F 2/4611 606/90 |
| 2008/0300601 A1* | 12/2008 | Fabian | ................. | A61B 17/025 606/90 |
| 2009/0030423 A1* | 1/2009 | Puno | ..................... | A61F 2/4611 606/86 A |
| 2009/0048604 A1* | 2/2009 | Milz | ..................... | A61F 2/4603 606/90 |
| 2009/0105773 A1* | 4/2009 | Lange | ................. | A61B 17/7062 606/86 A |
| 2009/0292316 A1* | 11/2009 | Hess | .................. | A61B 17/7065 606/249 |
| 2010/0069912 A1* | 3/2010 | McCormack | ......... | A61F 2/4611 606/90 |
| 2011/0009969 A1* | 1/2011 | Puno | ..................... | A61F 2/4611 606/94 |
| 2011/0190816 A1* | 8/2011 | Sheffer | .............. | A61B 17/7062 606/249 |
| 2012/0158063 A1* | 6/2012 | Altarac | .............. | A61B 17/7065 606/249 |
| 2012/0265305 A1* | 10/2012 | Oh | ........................ | A61F 2/4611 623/17.16 |
| 2013/0226240 A1* | 8/2013 | Abdou | ............... | A61B 17/7067 606/248 |
| 2016/0045333 A1* | 2/2016 | Baynham | ................ | A61F 2/446 623/17.16 |
| 2016/0166407 A1* | 6/2016 | Mackenzie | ............. | A61F 2/442 606/248 |
| 2017/0252073 A1* | 9/2017 | Salvermoser | ...... | A61B 17/7076 |
| 2019/0038434 A1* | 2/2019 | Saito | .................... | A61F 2/4611 |
| 2019/0380843 A1* | 12/2019 | Kim | ..................... | A61F 2/4611 |

* cited by examiner

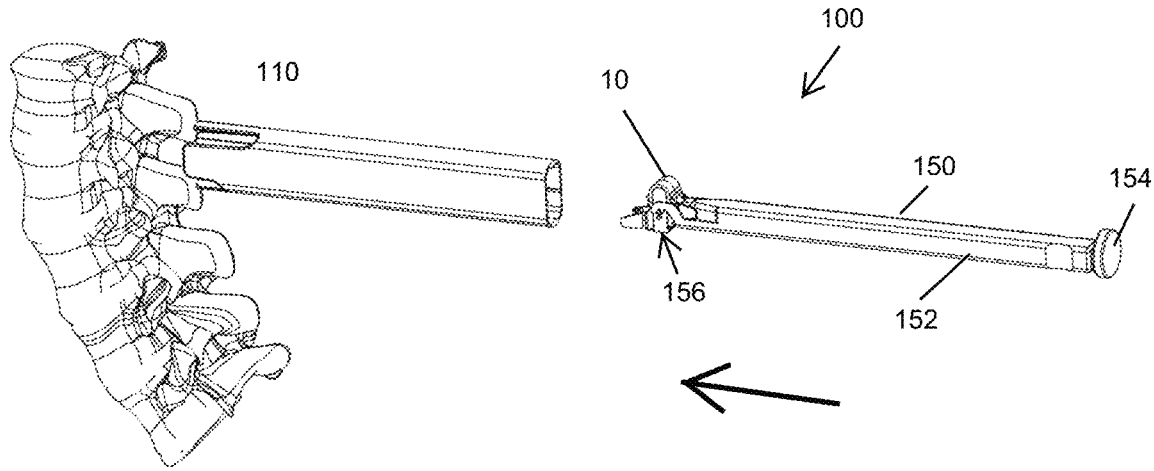
FIG. 2C
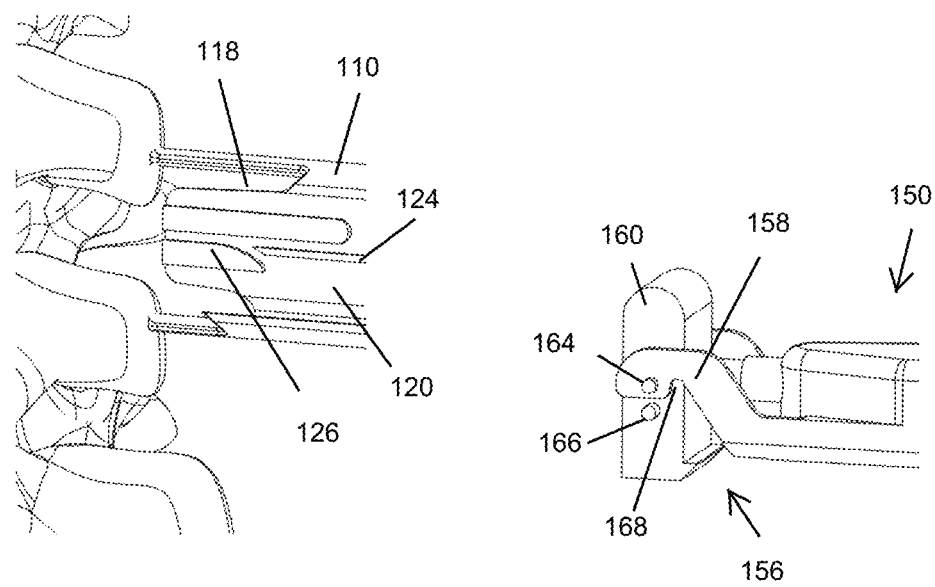
FIG. 2D  FIG. 2E

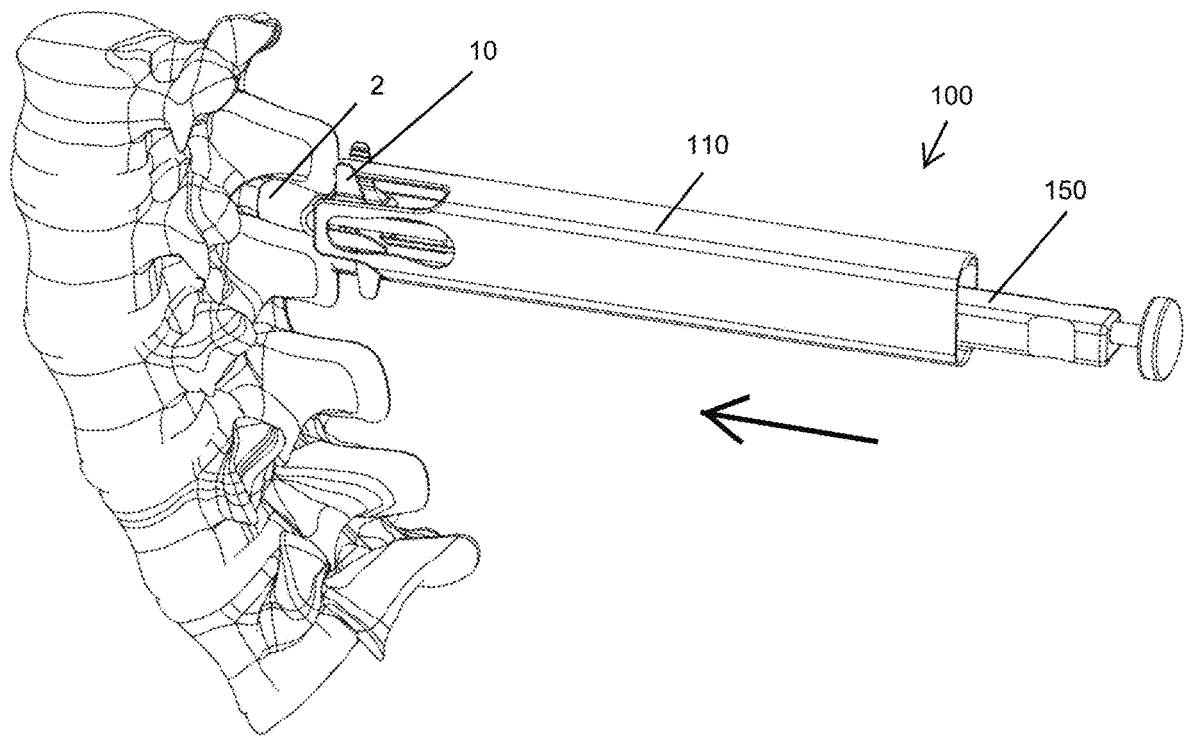
FIG. 2L
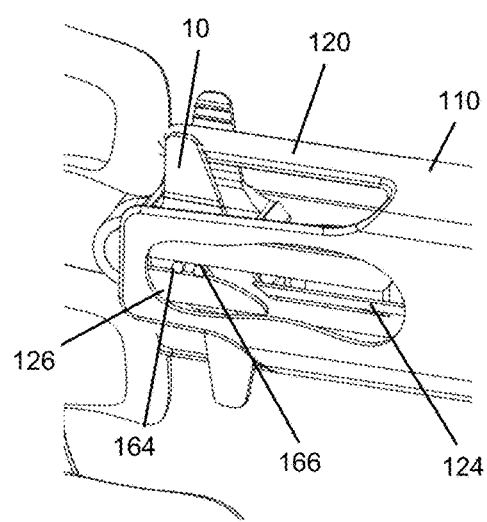 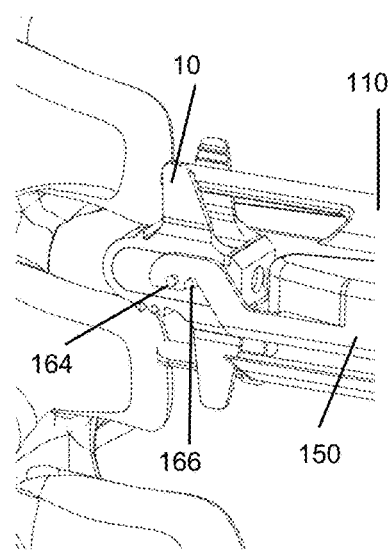
FIG. 2M           FIG. 2N

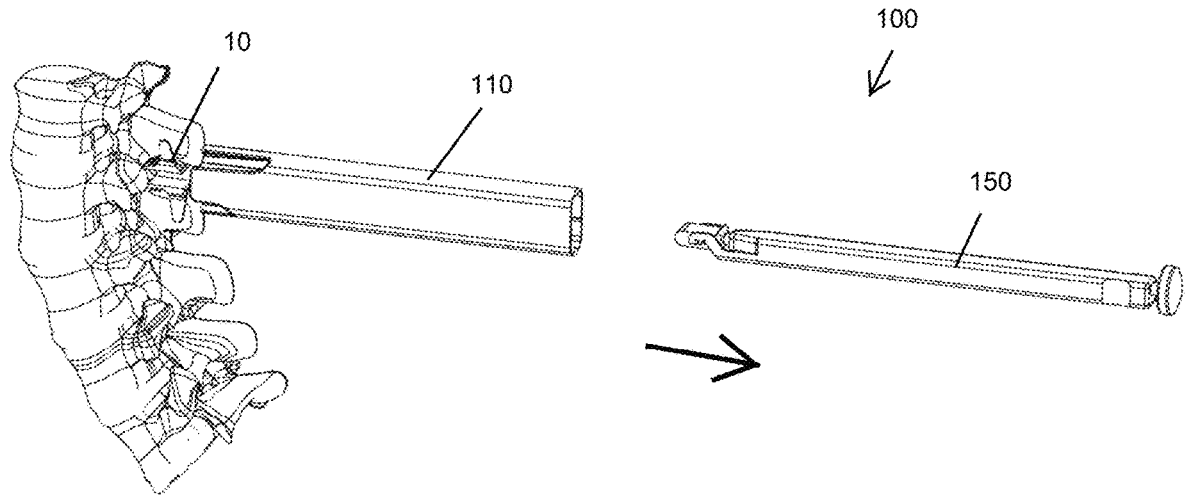
FIG. 2R
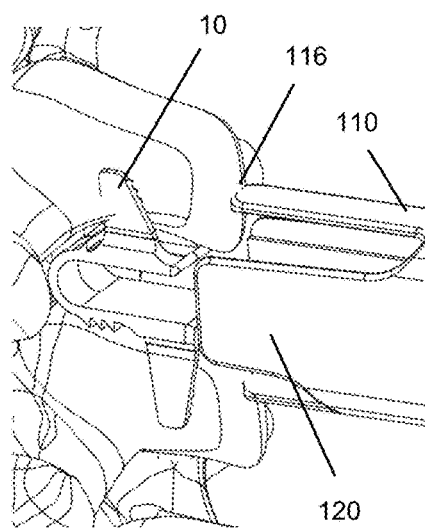
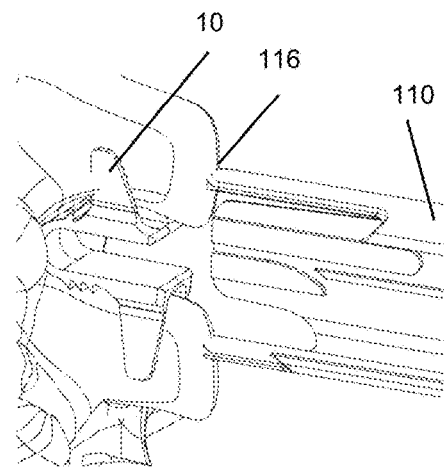
FIG. 2S  FIG. 2T

DELIVERY SYSTEMS FOR INTERSPINOUS, INTERLAMINAR STABILIZATION DEVICES AND METHODS OF USE

CROSS-REFERENCE TO RELATED APPLICATIONS

This application claims benefit of U.S. Provisional No. 62/530,561, filed Jul. 10, 2017, the entirety of which is herein incorporated by reference.

FIELD

The present disclosure relates to surgical instruments for delivering spinal stabilization devices and methods of use. More specifically, the present disclosure provides surgical delivery systems for spinal stabilization devices that are less invasive than currently available systems, and methods for using these systems with less invasive surgery techniques. These spinal stabilization devices may be, for example, interspinous and/or interlaminar stabilization devices.

BACKGROUND

Spinal instability is often attributed to undesirable excessive motion between vertebrae which can cause significant pain and morbidity. The instability may result from a number of causes, including abnormalities of the vertebrae, the intervertebral discs, the facet joints, or connective tissue around the spine. These abnormalities may arise from diseases, disorders or defects of the spine from trauma or bone degradation, such as osteoarthritis, or degenerative disc disease. When the spine becomes unstable, the vertebral column becomes misaligned and may allow micromotion between adjacent vertebrae. Vertebral misalignment and micromotion may result in wear of the vertebral bone surfaces and ultimately generate severe pain. These conditions are often chronic and create progressive problems for the sufferer.

Known treatments for spinal instability can include long-term medical management or surgery. Medical management is generally directed at controlling the symptoms, such as pain reduction, rather than correcting the underlying problem. For some patients, this may require chronic use of pain medications, which may alter the patient's mental state or cause other negative side effects. Surgical treatment typically includes decompression procedures to restore normal disc height, realign the column, and alleviate the pain.

Recently, a variety of interspinous vertebral stabilization devices have become available and have achieved clinical success. These devices are typically implanted between the spinous processes of two or more adjacent vertebrae. These devices may be motion-preserving, and provide various degrees of controlled movement of the spine while supporting the adjacent vertebrae. Other devices may be fusion-promoting. For instance, the fusion-promoting devices can be secured between adjacent spinous processes using a number of different mechanisms. For example, such devices can include sharp barbs or other surface projections that engage the bony surface of a spinous process. In addition, flexible ligaments or sutures can be placed around the implants to secure them to adjacent bone. In some cases, the devices may be rigidly attached to the spinous processes using a bone screw or other suitable bone anchor to prevent the interspinous stabilization device from migrating or slipping out of position. When the device is fastened to the spinous processes in this rigid manner, the device allows for fusion at this segment of the spine.

Some of these interspinous, interlaminar stabilization devices, such as those described in U.S. Pat. Nos. 5,645,599 and 7,922,750, for example, include an interspinous, interlaminar body portion having a U-shaped midsection for insertion into the interspinous, interlaminar space between adjacent vertebrae. In these and other interspinous, interlaminar stabilization devices, pairs of wings or brackets extending from the body portion and extending upwardly and/or downwardly create receiving spaces or slots for seating spinous processes of the adjacent vertebrae to keep these devices in place. To facilitate implantation and secure attachment of the wings of the devices to the spinous processes, it may be desirable to bend or crimp the wings to either expand the receiving space to receive the spinous process, or secure the wings to the spinous process.

By stabilizing the spinous processes in this way, significant stress may be taken off the intervertebral discs to alleviate pain, prevent disease progression or to improve conditions such as spinal stenosis. In addition, vertebral motion may be controlled without severely altering the anatomy of the spine. Further, treatments involving these interspinous, interlaminar vertebral devices are less invasive, may be reversible, and cause a less drastic alteration in the patient's normal anatomy and spinal function. These procedures may be used at an earlier stage of disease progression and, in some situations, may halt, slow down or even reverse the disease progression.

There is an existing need to be able to deliver these types of interspinous, interlaminar devices in a less invasive manner than is currently performed. The less invasive manner can encompass any delivery technique that further reduces trauma to the patient than what is currently achieved, up to and including minimally invasive type of procedures. Generally speaking, minimally invasive surgery (MIS) is a surgery minimizing surgical incisions to reduce trauma to the body. For example, the surgery can be performed through tiny incisions instead of one large opening. The potential advantages associated with a minimally invasive surgery are well studied and recognized. Examples of these associated advantages include reduced pain, a shorter hospital stay, earlier return to normal activities, less visible scarring, and fewer complications.

It is desirable to therefore provide instruments, systems and methods for delivering these types of interspinous, interlaminar stabilization devices in a less invasive than what is currently performed, up to and including in a minimally invasive manner.

BRIEF SUMMARY

The present disclosure provides various surgical instruments and delivery systems to properly implant spinous stabilization devices, such as for example, interspinous, interlaminar stabilization devices, in a less invasive manner than what is currently performed. Methods for using these surgical instruments and delivery systems are also provided.

According to one aspect of the disclosure, a delivery system to properly implant interspinous, interlaminar stabilization devices in a minimally invasive manner is provided. The delivery system comprises a working sleeve having a hollow elongate body, a proximal end having an opening for receiving a surgical instrument, and a distal end for engaging a bony surface. An insertion instrument for delivering an interspinous, interlaminar stabilization device through the working sleeve and to an implantation site between adjacent spinous processes is also provided. The insertion instrument may have a swivel arm for holding the device in a first, low profile configuration for insertion through the working sleeve and a second, upright configuration for delivery to the implantation site. This second, upright configuration may be angled up to about 90 degrees relative to the first, low profile configuration. A trocar and a crimping plier may also be provided with the delivery system.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 2A-2T illustrate an exemplary embodiment of a delivery system of the present disclosure, and method of using the delivery system to implant the interspinous, interlaminar stabilization device of FIG. 1A, in which:

FIG. 2A shows a working sleeve with trocar assembly;

FIG. 2C shows an exploded view of the working sleeve of FIG. 2A and inserter instrument with device;

FIGS. 2D and 2E show enlarged, detailed views of the working sleeve and inserter instrument of FIG. 2C, respectively; and FIGS. 2F-2T show a method of delivering the device through the working sleeve using the inserter instrument of FIG. 2C.

FIGS. 4A-4G illustrate still another exemplary embodiment of a delivery system of the present disclosure, and method of using the delivery system to implant the interspinous, interlaminar stabilization device of FIG. 1A, in which;

FIG. 4A shows a working sleeve with a trocar assembly;

FIG. 4B shows the working sleeve of FIG. 4A with an insertion instrument and attached device;

FIG. 4C shows the insertion instrument and attached device of FIG. 4B without the working sleeve;

FIGS. 4D, 4E and 4F illustrate a method of delivering the interspinous, interlaminar device of FIG. 4A; and FIG. 4G shows the insertion instrument and attached device of FIG. 4F without the working sleeve.

DETAILED DESCRIPTION

The present disclosure provides various surgical instruments and delivery systems to properly implant spinous stabilization devices, such as interspinous, interlaminar stabilization devices. According to one aspect of the disclosure, these surgical instruments and delivery systems are configured to allow the devices to be delivered in a less invasive manner than is currently performed. Methods of using these surgical instruments and delivery systems in a less invasive manner, including, but not limited to, delivery by minimally invasive surgery (MIS), are also provided. For example, the surgical instruments and delivery systems may be utilized in an endoscopic procedure.

The surgical instruments and delivery systems of the present disclosure are configured for less invasive delivery of spinal stabilization devices, such as implantable interspinous, interlaminar stabilization devices of the type having a U-shaped midsection for interspinous, interlaminar placement between adjacent vertebrae, and/or pairs of brackets or wings defining a receiving space for seating a spinous process of one of the vertebrae. Examples of such implantable interspinous, interlaminar stabilization devices are described in U.S. Pat. Nos. 5,645,599, 7,922,750, 9,370,382 and in U.S. Patent Application Publication No. 2017/0027619, as well as others.

Figure 1A:
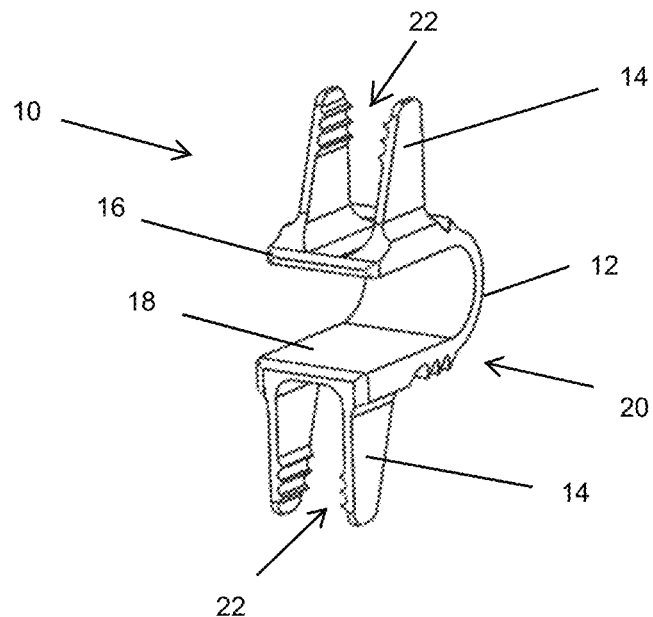
FIG. 1A illustrates a perspective view of an implantable interspinous, interlaminar stabilization device of the prior art.
Figure 1B:
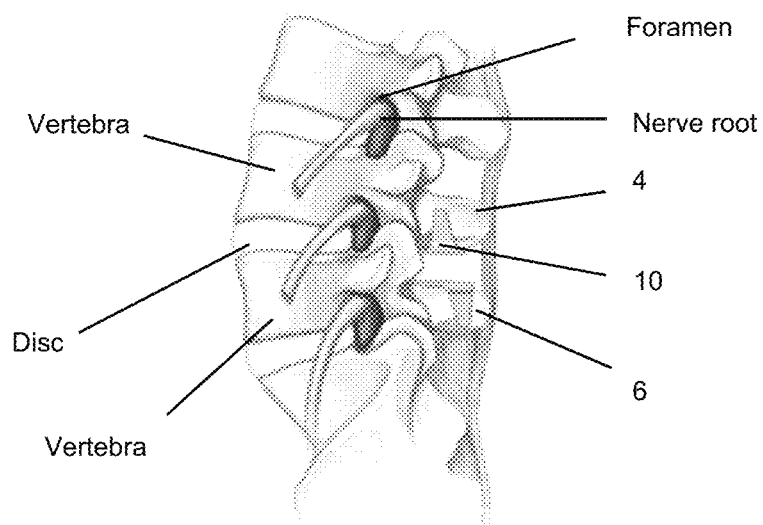
FIG. 1B illustrates the implantable interspinous, interlaminar stabilization device of FIG. 1A in situ.

FIG. 1A shows an exemplary implantable interspinous, interlaminar stabilization device 10 of the prior art suitable for use with the instruments and delivery systems of the present disclosure. The device 10 may be configured for placement between the spinous processes of adjacent vertebrae. The device 10 may have various shapes and thicknesses, and can be produced from a variety of different materials. In one embodiment, the device 10 may include a midsection 12 extending between a superior section 16 and an inferior section 18. When implanted in a patient, the superior section 16 is configured to contact a portion of a first spinous process 4, while the inferior section 18 is configured to contact a portion of a second, adjacent spinous process 6, as shown in FIG. 1B.

In one embodiment, the midsection 12, inferior section 16, and superior section 18 may together form a substantially U-shaped body 20, as shown. The device 10 may be configured to be flexible and/or bendable, such as, for example, by providing an extendable and/or compressible midsection 12. The midsection 12 can act as a flexible hinge, allowing the superior section 16 and inferior section 18 to move away from or towards one another. Furthermore, the U-shaped body enables the device 10 to be positioned, or fitted, interlaminarly after implantation, thereby enhancing the stabilization of the adjacent vertebrae.

To engage the spinous processes of adjacent vertebrae, the device 10 may be provided with a pair of wings, lateral walls or brackets 14 that extend from the inferior and superior sections 16, 18, as shown in FIG. 1A. Each of the pair of lateral walls 14 defines a stirrup 22 for receiving a spinous process. The device 10 can be provided with lateral walls 14 of various sizes or heights to accommodate variations in patient anatomy. Likewise, the lateral walls 14 of different devices 10 may be provided at differing locations along the length of the inferior section 18 or superior section 16. The surgeon can thus select a suitably shaped and sized device 10 depending on the particular vertebral level to be supported and the anatomy of the patient.

Further, the lateral walls 14 may also be adjustable with respect to the device 10. For example, in one embodiment, the lateral walls 14 may be formed of a malleable material such that, after implantation, the surgeon may compress the lateral walls 14 together to reduce the gap between the lateral walls 14, thereby securely fixing the device 10 to a spinous process located therein. In addition, the lateral walls 14 may be spread apart to facilitate insertion. The lateral walls 14 may be compressed or spread apart, for example, using surgical pliers or forceps.

In some embodiments, the lateral walls or brackets 14 can also include an aperture for receiving a bone fastener to rigidly fix the brackets 14 to the spinous process. Such fastening members can ensure that the brackets 14 are pressed flat and/or securely against the spinous process in order to avoid any play of the brackets 14 with respect to the spinous process. As such, the device 10 may act as a fusion-promoting device when the implantable device 10 is fastened to the spinous process in this manner.

Suitable bone fasteners may comprise a two-component type that includes a bolt and nut assembly such as the type described in U.S. Pat. No. 7,922,750 that allows a tight, secure connection with the spinous process. In some embodiments, the tight, secure connection between the device 10 and adjacent spinous processes will limit movement at the selected vertebral level, thereby promoting fusion at that level.

As mentioned, the benefits and advantages of treatments involving these kinds of interspinous, interlaminar stabilization devices can only be realized if the interspinous, interlaminar stabilization devices are properly implanted within the patient. This requires the surgeon to assess the proper size (e.g., height and depth) of the interspinous, interlaminar space so that the appropriately sized device is selected and implanted. Additionally, adjustments to the wings of these devices may be needed prior to implanting in order to open up the receiving space and accommodate the anatomy of the spinous process. Once implanted, adjustments may also need to be made to the wings to crimp them onto the spinous process.

By way of introduction, prior to insertion of any interspinous, interlaminar stabilization device, the implant site may need to be prepared. Selection of the appropriate implant size is essential towards achieving proper function of the device and good clinical results. Device trials may be utilized to determine the appropriate implant size. For example, a set of trials covering the range of implantable device sizes can be provided, usually in a sterile tray or package, corresponding to the range of device sizes available. In one example, the device size may range from about 8 to about 16 mm in height. The trial instrument may be employed to evaluate proper contact with the spinous process and amount of interspinous distraction. The surgeon would typically start with the smaller sized trials and sequentially advance in size, until the proper size is determined. The ideal implant size may take into account a desirable amount of facet distraction. For example, for one type of interspinous, interlaminar stabilization device, the ideal implant size may achieve 1-2 mm facet distraction. The trial should be able to be advanced linearly to the mid-level of the facet joint, without rotation, angulation or rocking of the trial, which might indicate a possible anatomic obstruction, or that the device may not function properly after implantation. If desired, the trial can be advanced using a mallet in a direct linear fashion to its final position before any attempt to implant the device itself.

Figure 2A:
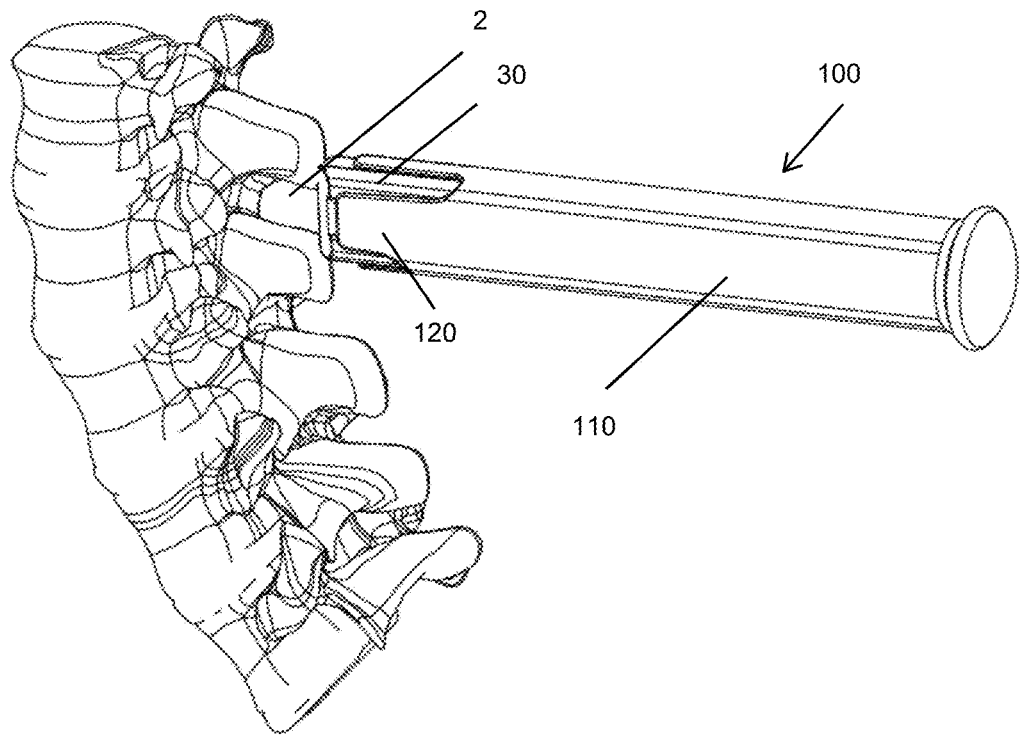

Turning now to the drawings, FIGS. 2A-2T illustrate an exemplary embodiment of a delivery system 100 in accordance with one aspect of the present disclosure, and methods of using this delivery system 100 to implant an interspinous, interlaminar stabilization device 10 similar to the one shown in FIG. 1A, in a minimally invasive manner. Generally speaking, the delivery system 100 is a tubular delivery system through which instruments and devices can pass. The delivery system 100 may comprise a working sleeve or cannula 110 into which a variety of surgical instruments may be inserted for delivering the device 10 to its proper destination. According to one aspect, a trocar 130 may be provided with the system 100. In a first step of the procedure, the trocar 130 may be inserted into the working sleeve 110 of the system 100 and together, both instruments may be inserted toward the implantation site 2 as shown in FIG. 2A. The trocar 130 may be used to help impact the working sleeve 110 in between the spinous processes of the implantation site 2.

As shown, the working sleeve or delivery tube 110 may have a hollow tubular body 112 extending between a proximal, or an instrument insertion end 114, and a distal, or a bone engagement end 116. The bone engagement end 116 may comprise a series of slots or cutaway portions 118 between which are finger projections 120. Collectively, these finger projections 120 and cutaway portions 118 create a shaped grasping end to allow the delivery tube 110 to be positioned in the proper location for delivering the device 10.

Figure 2B:
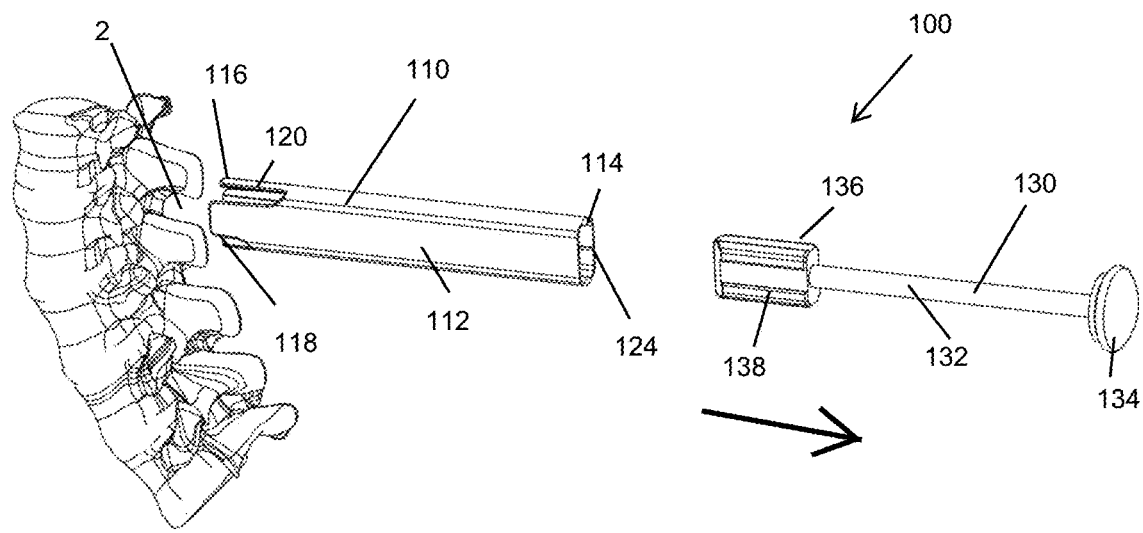
FIG. 2B shows an exploded view of the working sleeve and trocar assembly of FIG. 2A.

Within the tubular body 112, guide rails 124 may be provided for engaging and aligning the head portion 136 of the trocar 130, as shown in FIG. 2D. The head portion 136 may further include grooves 138 for engagement with the guide rails 124 within the delivery tube 110. As further shown in FIG. 2B, the trocar head portion 136 may extend from an elongate shaft 132 which terminates into a handle 134. This handle 134 enables the user to insert and remove the trocar 130 from the working sleeve 110, a step shown in FIG. 2B after the working sleeve 110 has been properly positioned at the implantation site 2.

FIG. 2C shows a device insertion instrument 150 of the delivery system 100 being inserted with an attached device 10 into the working sleeve 110. The insertion instrument 150 may be configured with an elongate shaft 152 between a handle 154 and an operative end 156. As shown, the operative end 156 of the insertion instrument 150 may be configured to engage and hold onto the interspinous, interlaminar device 10 being delivered. FIG. 2E shows in greater detail the operative end 156 of the insertion instrument 150, without the device 10 attached. The insertion instrument 150 may be configured with brackets 158 holding a swivel arm 160. This swivel arm may be configured to pivot up to about 90 degrees from a first pin 164 extending out from both sides and holding it to the brackets 158. A rounded or shaped end of the swivel arm 160 is configured to receive the interspinous, interlaminar device 10 as shown in FIG. 2C. As shown in FIGS. 2G and 2H, in a cutaway view of the working sleeve 110, the guide rails 124 are configured to engage the first pin 164 as the insertion instrument 150 is inserted through the working sleeve 110. A second pin 166 is provide near the first pin 164, and as the swivel arm 160 moves to its final position, this second pin 166 may engage a notch 168 on the brackets 158, thereby stopping further movement and locking the swivel arm 160, as will be described below.

Figure 2F:
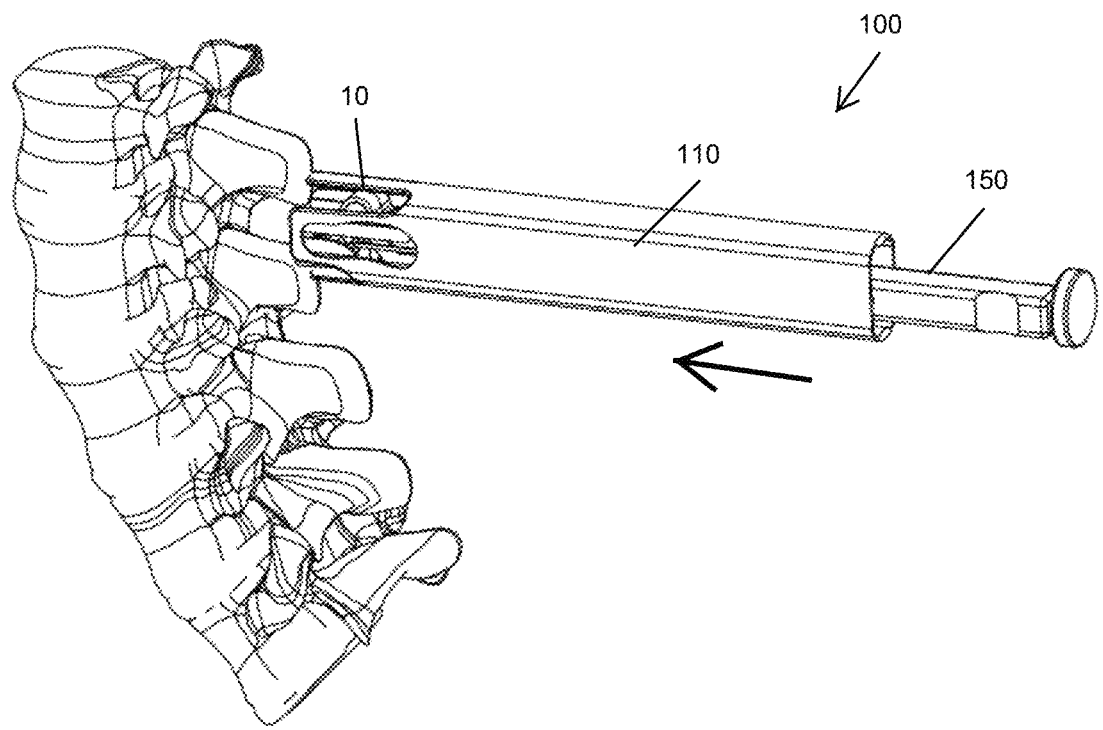
Figure 2G:
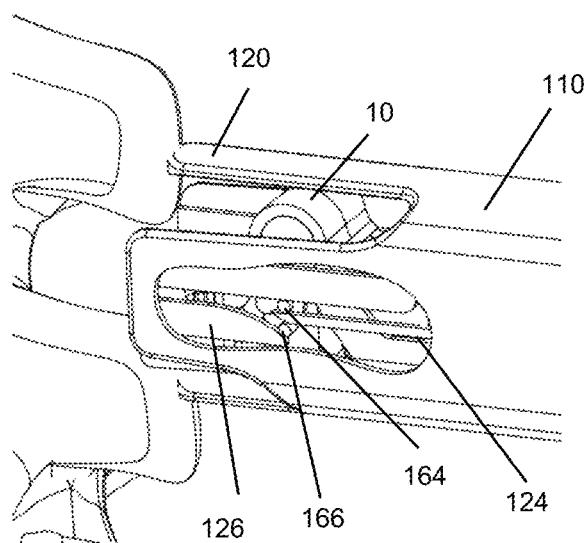
Figure 2H:
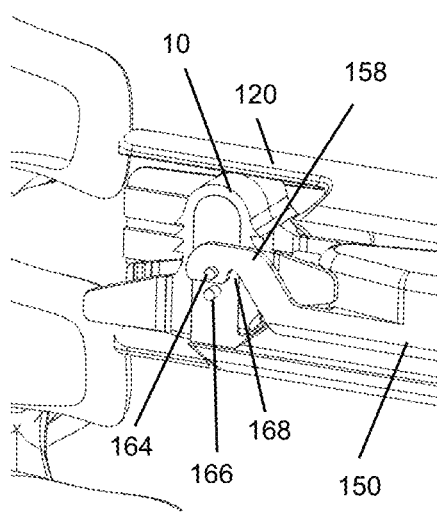
Figure 2I:
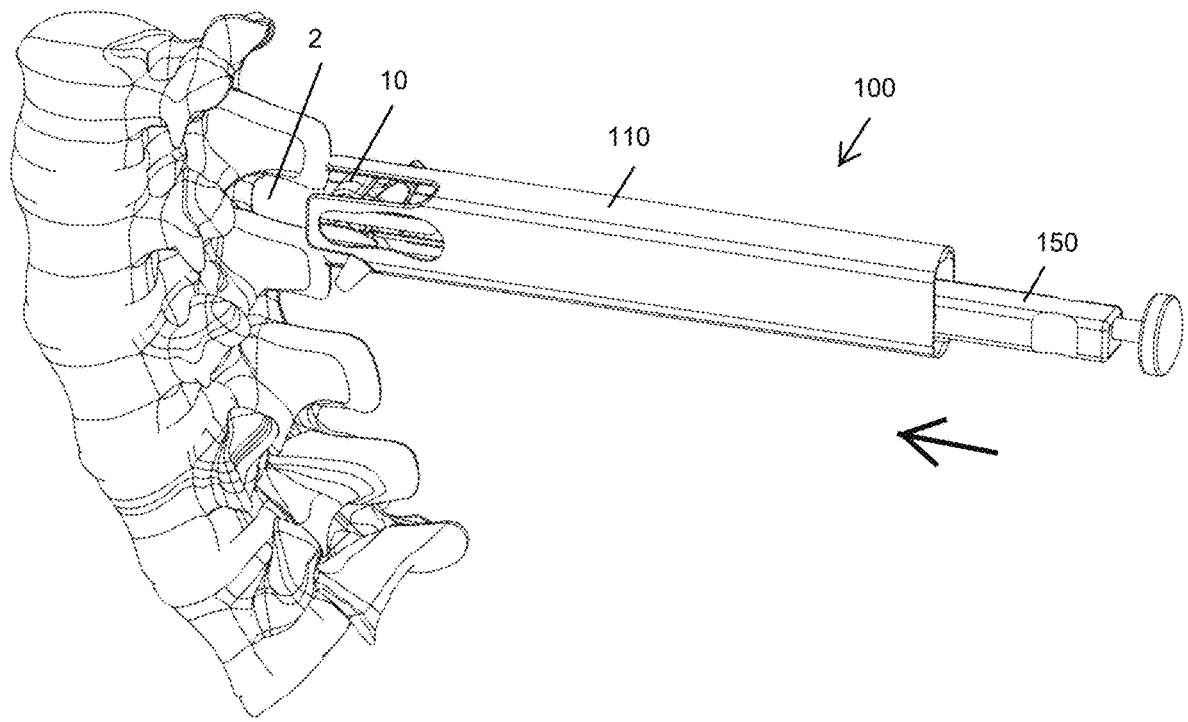
Figure 2J:
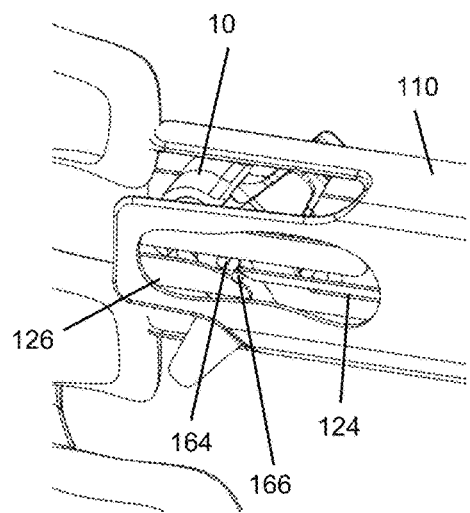
Figure 2K:
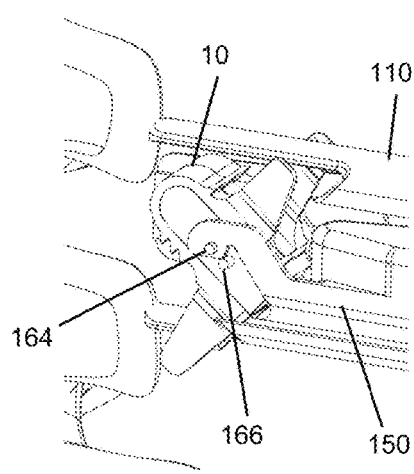

FIGS. 2F-2T illustrate the steps of inserting the device 10 into the working sleeve 110 and to the implantation site 2. As shown and described above, the device 10 may be attached to the swivel arm 160 of the insertion instrument 150, as shown in FIG. 2C, in a first, low-profile configuration. As shown in FIGS. 2F to 2H, during insertion of the insertion instrument 150 into the working sleeve 10, the first pin 164 engages the guide rails 124 within the tubular body 112 of the delivery tube 110. This allows proper alignment of the insertion instrument 150 relative to the working sleeve 110 during insertion. Once the first pin 124 on the insertion instrument 150 reaches the end of the guide rails 124, the further advancement of the insertion instrument 150 causes the first pin 164 and eventually the second pin 166 to slide against a shoulder ramp 126 on the inside of the tubular body 112, causing the swivel arm 160 and the associated device 10 attached thereto to swivel, or angularly adjust, as evidenced by the movement of the first pin 164 relative to the second pin 166, as shown in FIGS. 2I to 2K. The device 10 is now in a second, upright configuration.

Figure 2O:
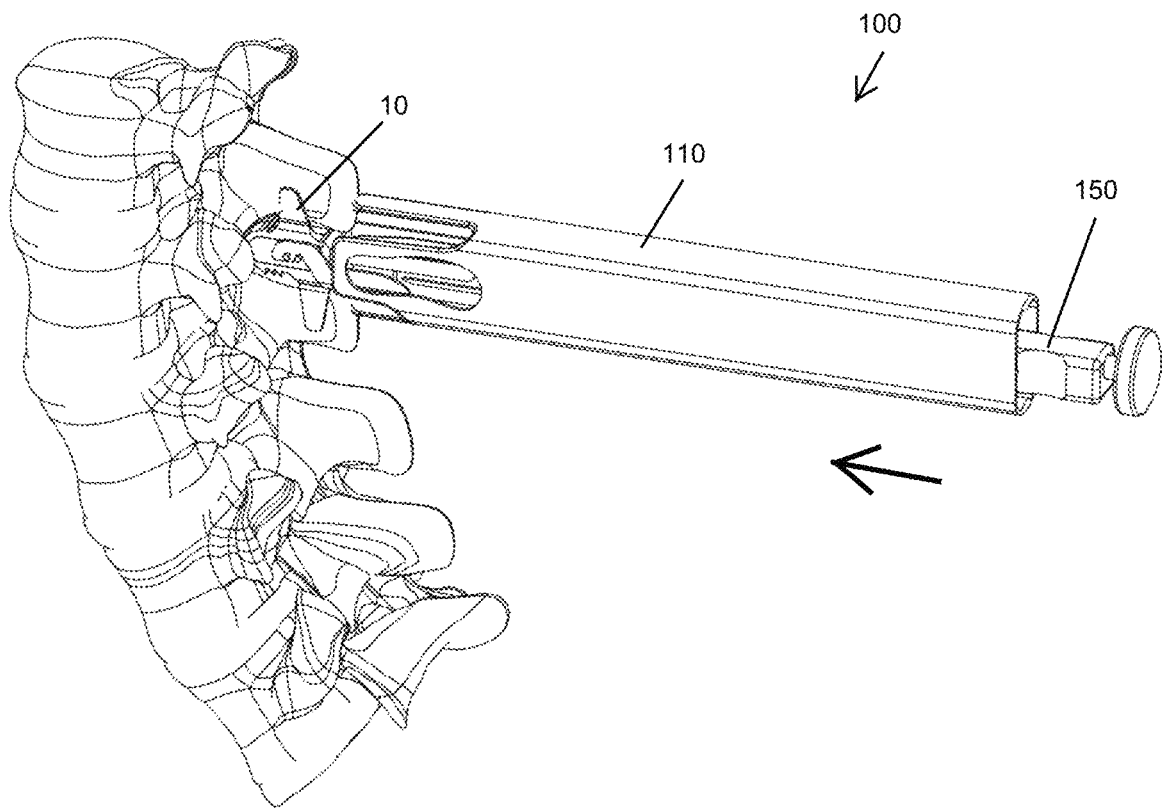
Figure 2P:
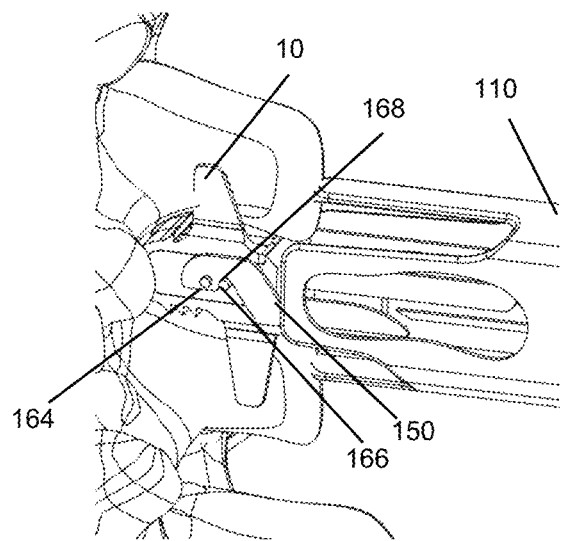
Figure 2Q:
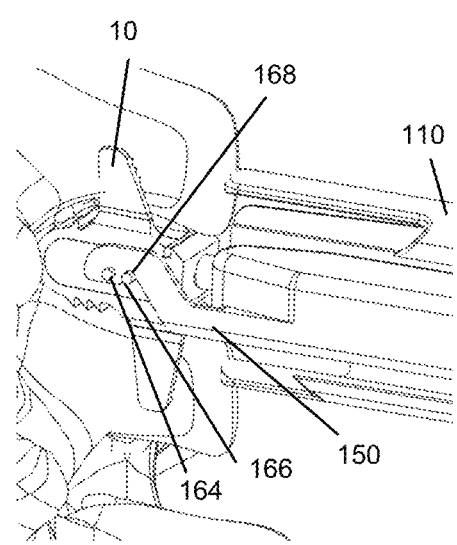

Once the swivel arm 160 has pivoted up to about 90 degrees, the two pins 164, 166 are in horizontal alignment, with the second pin 166 engaged with the notches 168 on the brackets 158 of the insertion instrument 150, as shown in FIGS. 2L to 2N. The engagement of the second pin 166 within the notches 168 locks the swivel arm 160 in place, and prevents further movement. Now fully locked, FIGS. 2O to 2Q show that further advancement of the insertion instrument 150 can urge the device 10 into the implantation site 2. After the interspinous, interlaminar device 10 has been properly seated, the insertion instrument 150 may be removed, as shown in FIGS. 2R to 2T.

Figure 3A:
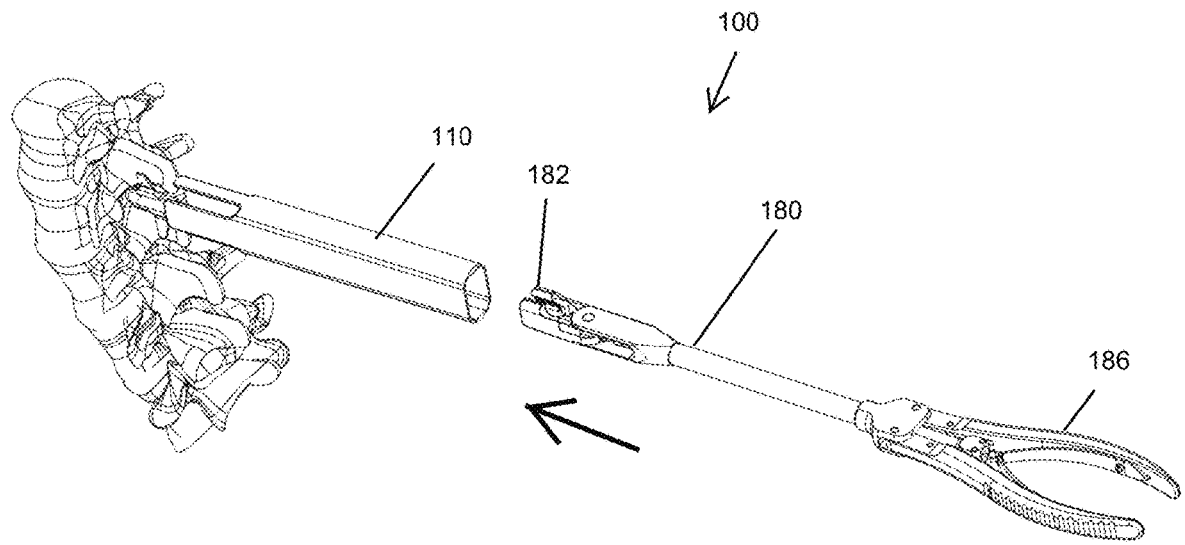
FIGS. 3A-3M illustrate a method of crimping the implanted device of FIG. 2T using the working sleeve of FIG. 2A and an exemplary embodiment of a crimping plier of the delivery system of the present disclosure.
Figure 3B:
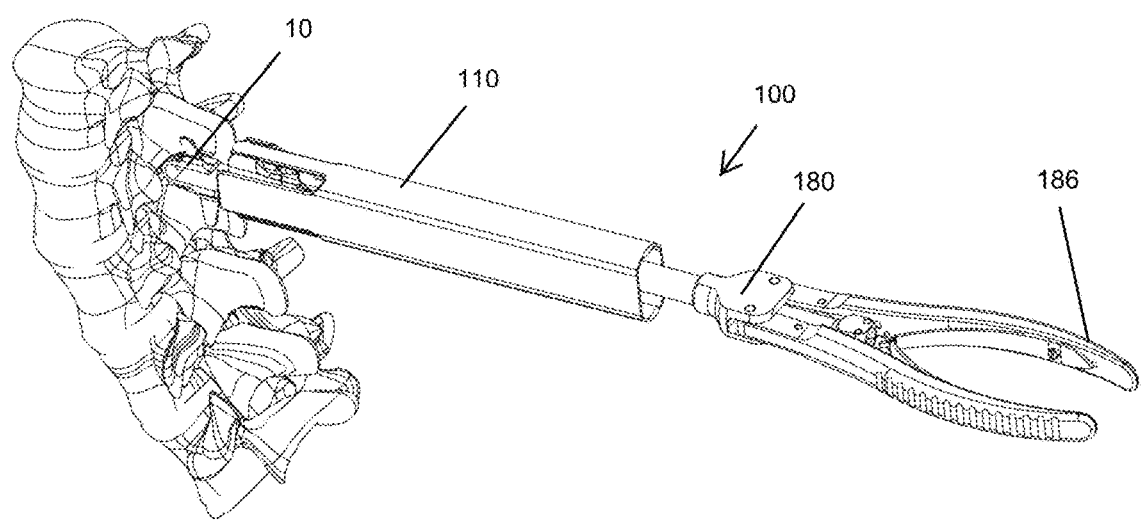

FIGS. 3A-3M illustrate a method of crimping the implanted device 10 using the same working sleeve 110 described above and an exemplary embodiment of a crimping plier 180 of the delivery system 100 of the present disclosure. As shown in FIG. 3A, once the insertion instrument 150 has been removed, what remains is the inserted device 10 and the working sleeve 110. According to an aspect of the disclosure, a crimping plier 180 may be provided with the delivery system 100 for crimping the brackets 14 of the device 10 onto the spinous processes, as previously described above. The crimping plier 180 may operate in a similar manner to the one described in U.S. Pat. No. 8,834,482, the contents of which are incorporated in entirety by reference. The crimping plier 180 may be configured to be inserted through the working sleeve 110, as shown in FIG. 3B, and onto the brackets 14 of the device 10.

Figure 3C:
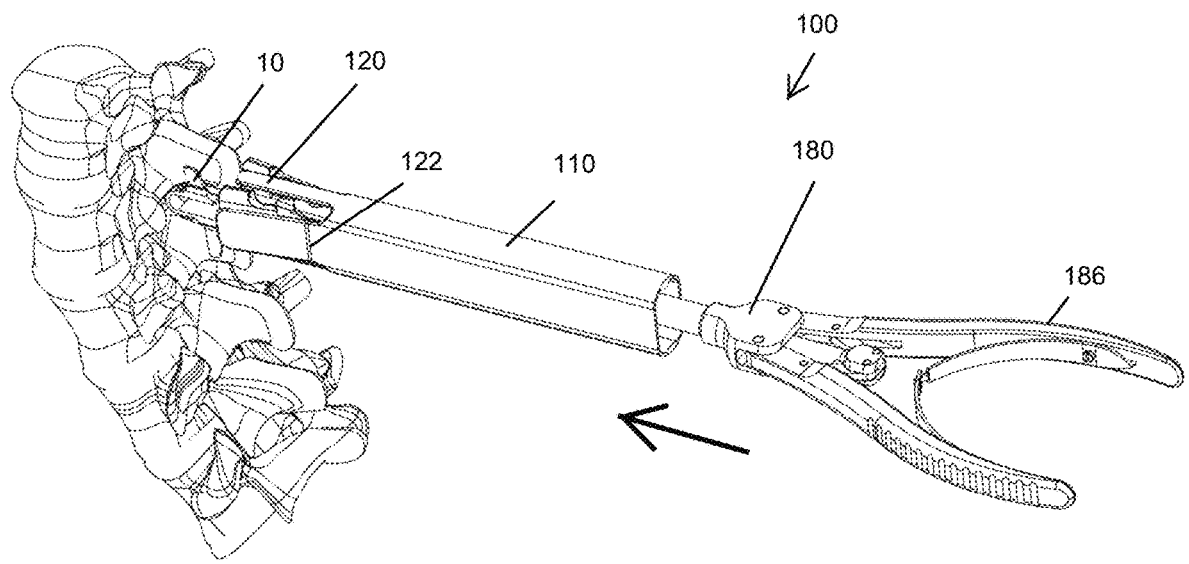
Figure 3D:
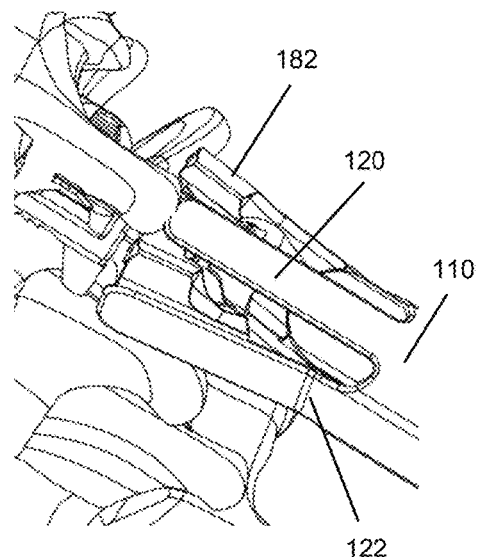
Figure 3E:
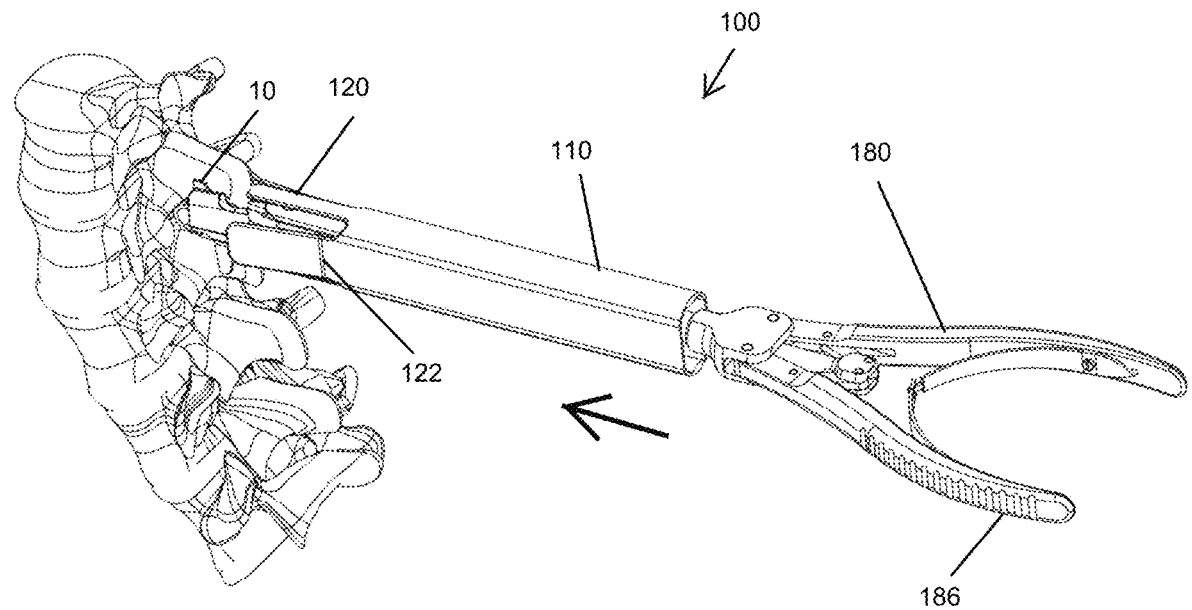
Figure 3F:
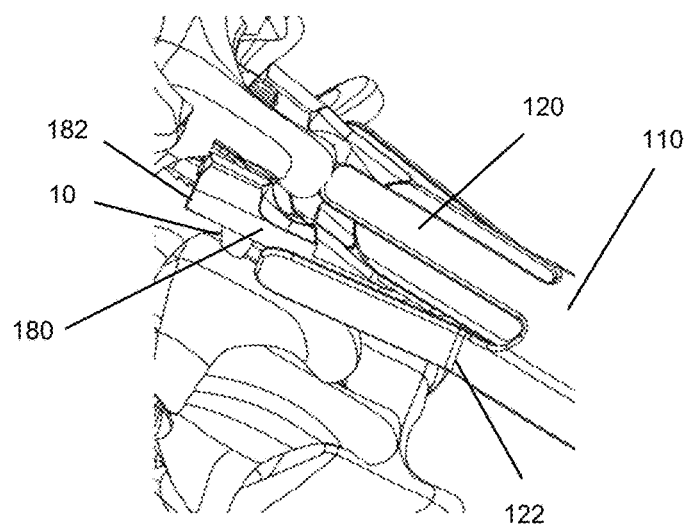
Figure 3G:
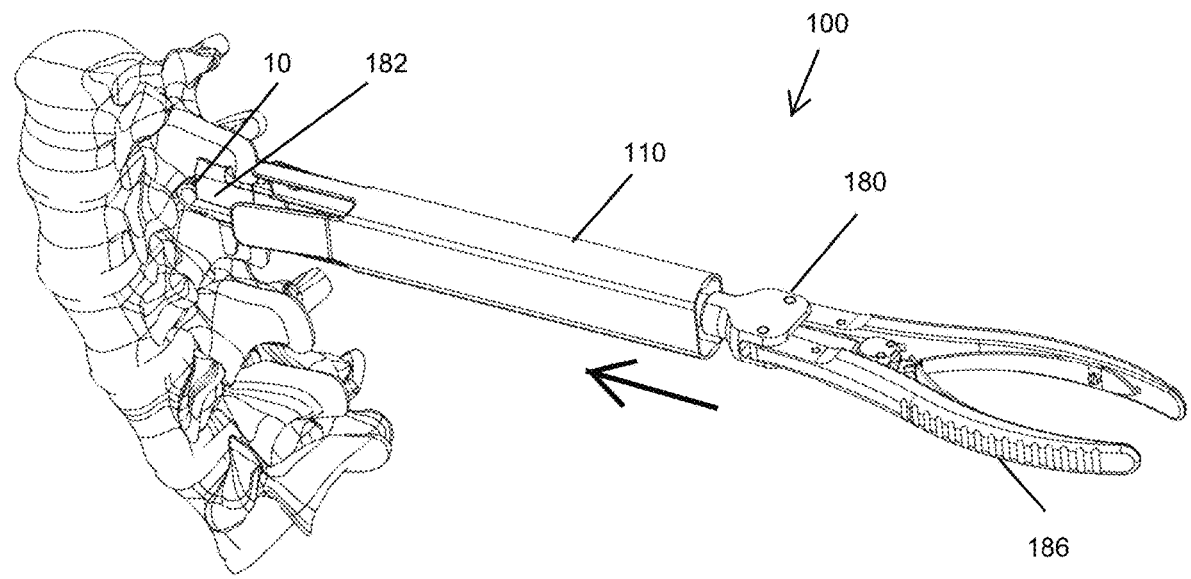
Figure 3H:
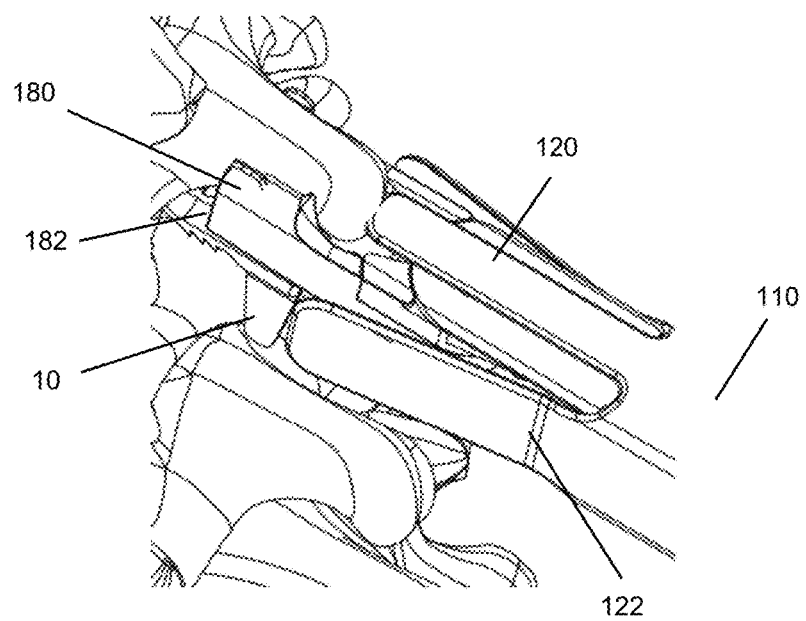
Figure 3I:
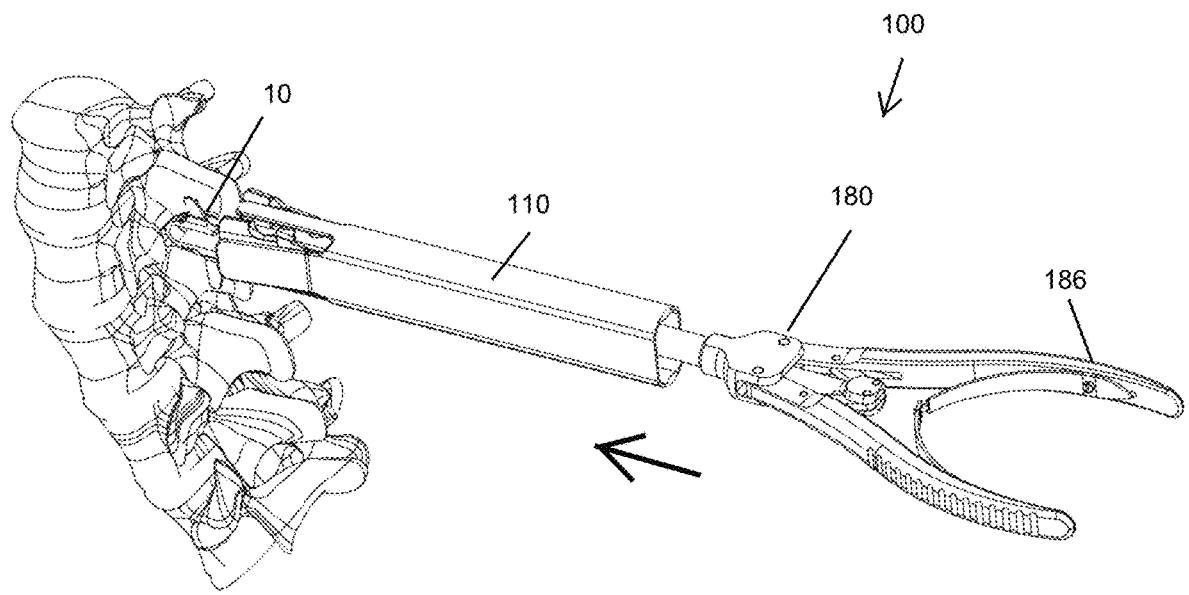
Figure 3J:
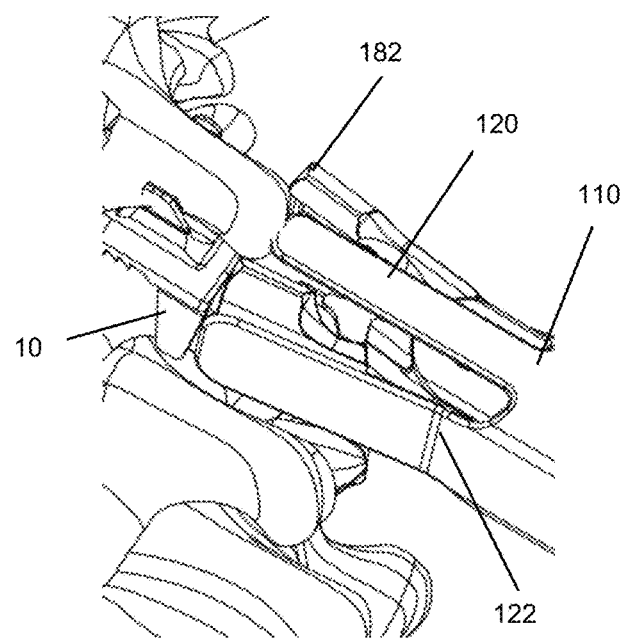
Figure 3K:
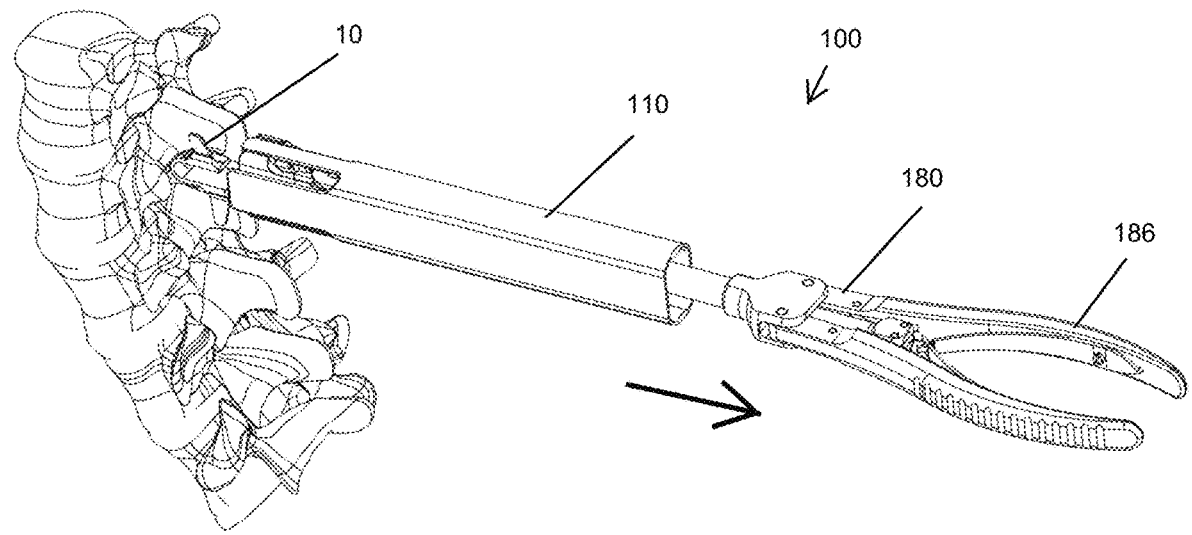
Figure 3L:
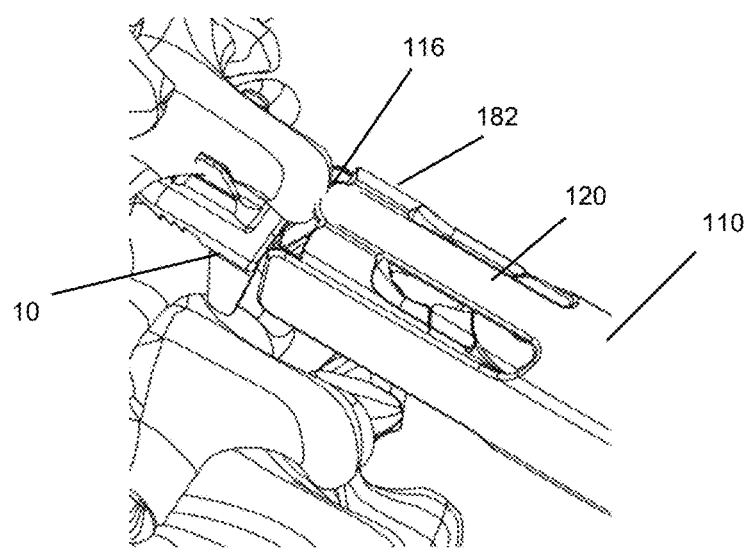
Figure 3M:
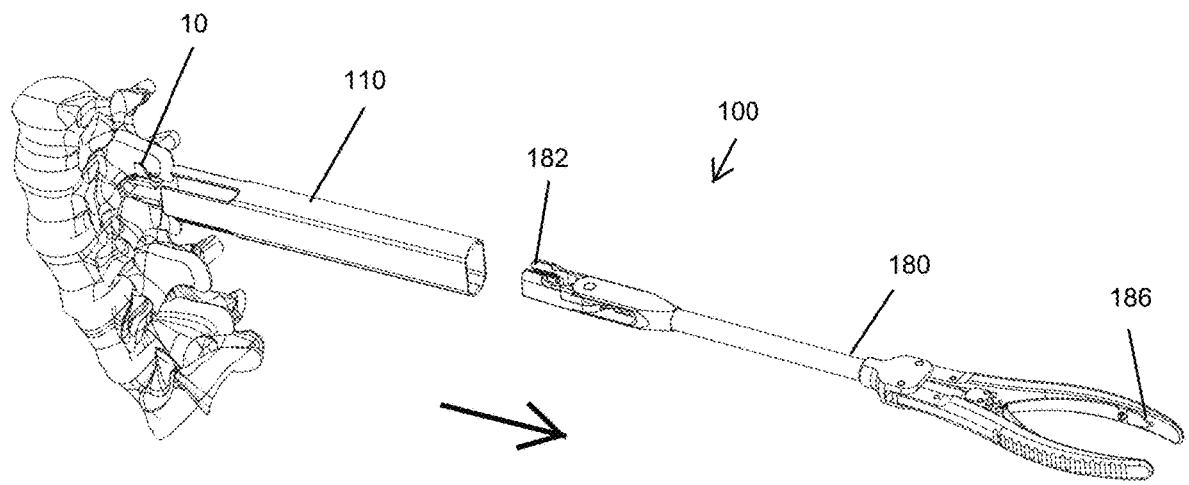

In order to allow movement of the working end of the plier 180, in one embodiment, the finger projections 120 of the working sleeve 110 may be spread apart for additional space. As shown in FIGS. 3C and 3D, the tip 182 of the crimping plier 180 can spread the distal or bone engaging end 116 of the working sleeve 110. According to one aspect, the finger projects 120 may be scored and contain scored sections 122 to allow it to bend outwardly, as shown. The added spatial clearance allows the crimping plier 180 to be placed on the device 10 as shown in FIGS. 3I and 3J, and by squeezing the handles 186 of the crimpling pliers 180, the tip 182 of the crimping plier 180 squeeze the brackets 14 of the device 10 onto the spinous process. Upon completion, the crimping pliers 180 can be removed from the device 10 and consequently the working sleeve 110, as shown in FIGS. 3K to 3M, leaving behind a completely seated and crimped interspinous, interlaminar device 10. Finally, the working sleeve 110 of the delivery system 100 can be removed from the surgical site.

FIGS. 4A-4G illustrate another exemplary embodiment of a delivery system 200 in accordance with another aspect of the present disclosure, and methods of using this delivery system 200 to deliver an interspinous, interlaminar device 10 in a minimally invasive manner. Generally speaking, the delivery system 200 is a tubular delivery system through which instruments and devices can pass. Delivery system 200 may include a working sleeve 210 and a trocar 230 similar to delivery system 100 described above. Like working sleeve 110, the working sleeve of system 200 also includes a hollow tubular body 212 extending between distal end 216 and proximal end 214. The distal end 216 may also include finger projections 220 and cutaway portions 218 for grasping the bony surface around the spinous processes 4, 6 at the implantation site 2.

Figure 4A:
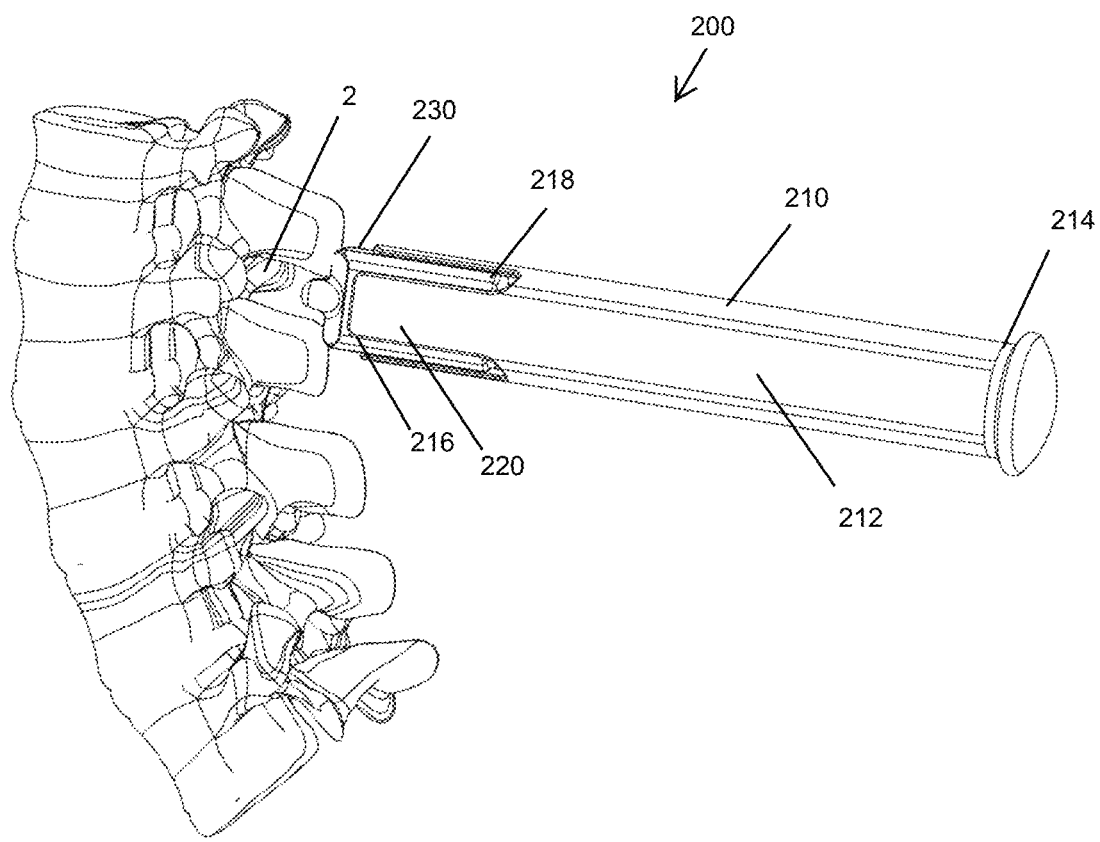
Figure 4B:
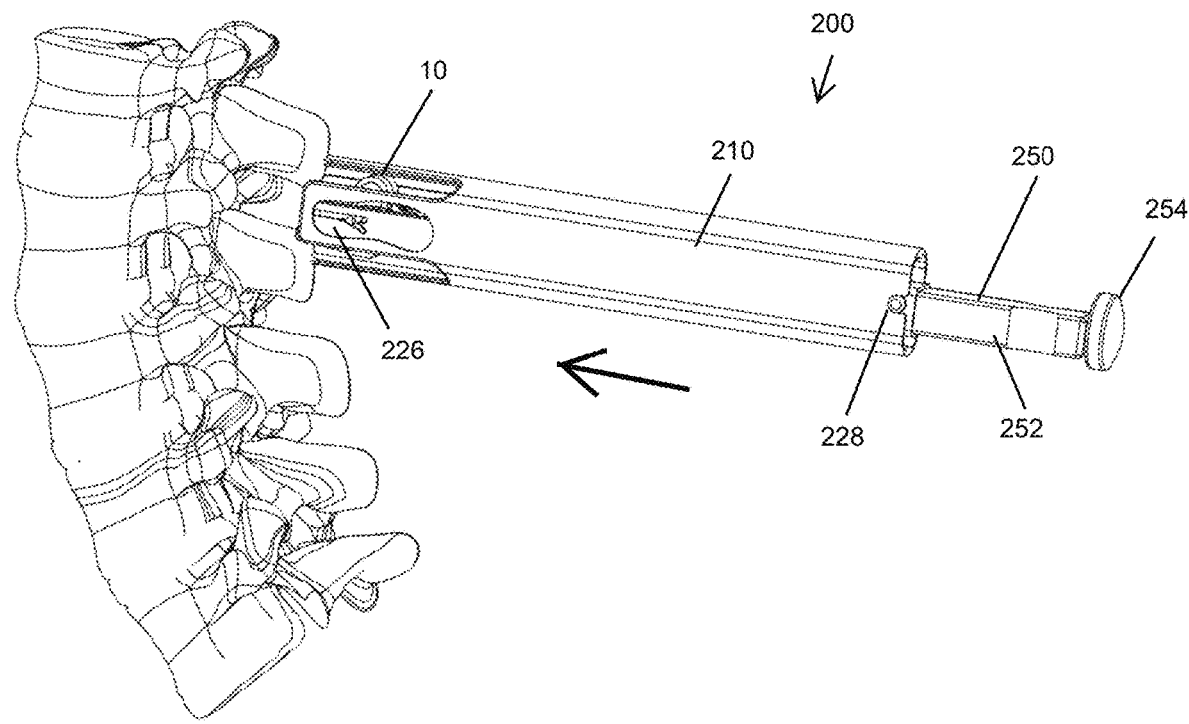
Figure 4C:
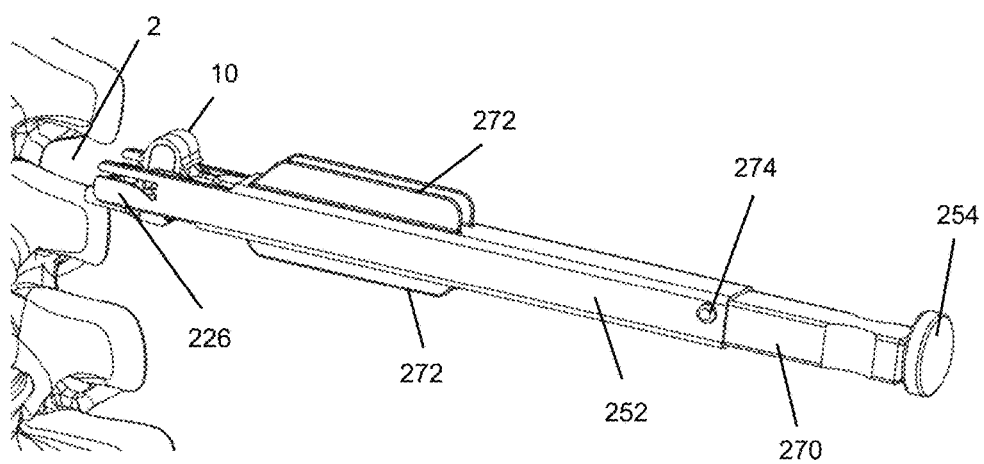

However, unlike working sleeve 110, the present working sleeve 210 has no internal guide rails, has a smooth interior, and therefore is a passive component of the delivery system 200, providing no mechanical function as with the other embodiment of the working sleeve 110. Instead, the various other surgical instruments of the delivery system 200 may be configured with guide features. For instance, trocar 230 may be provided with its own guiding surface features in one example (not shown). In one aspect, the insertion instrument 250 of the delivery system 200 may include guide fins 272, as shown in FIG. 4C. This allows the insertion instrument 250 to be correctly advanced through the working sleeve 210 as shown in FIG. 4B. Additionally, insertion instrument 250 may have a swivel arm 260 and pins 264, 266 similar to insertion instrument 150 described above. However, as shown in FIG. 4C, the insertion instrument 250 includes a further mechanism to swivel the arm 260.

Figure 4D:
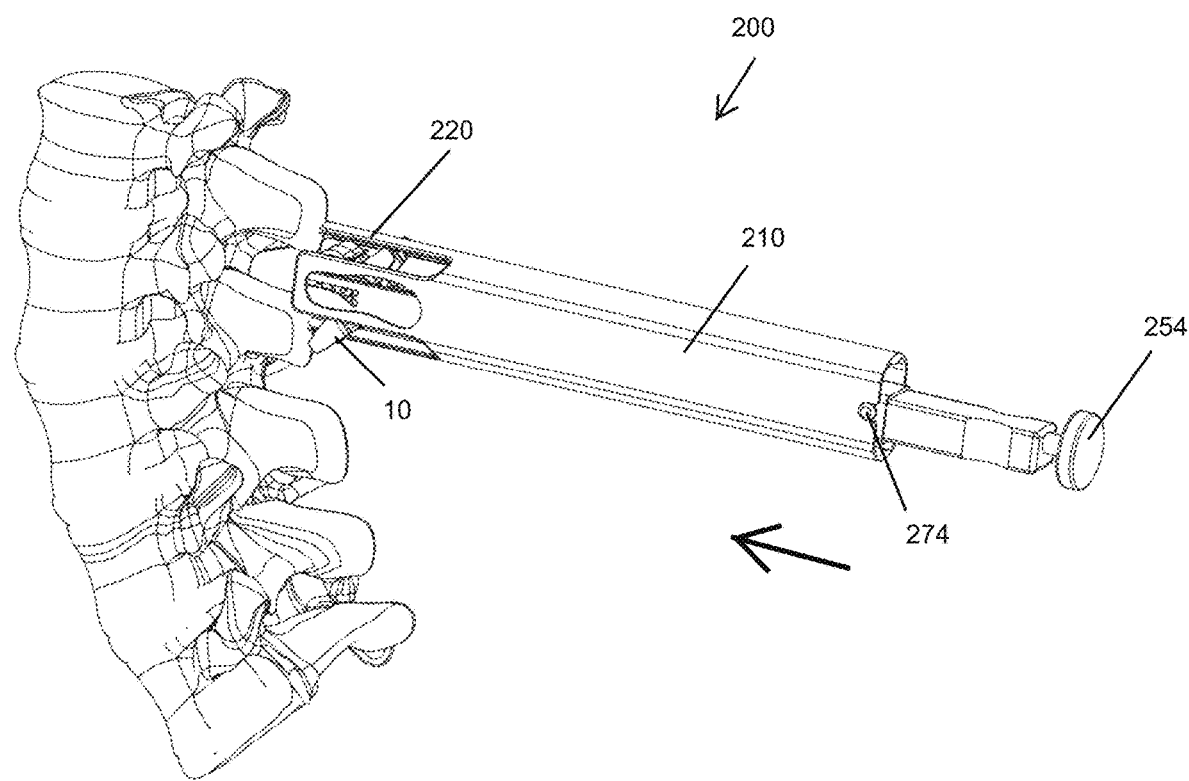
Figure 4E:
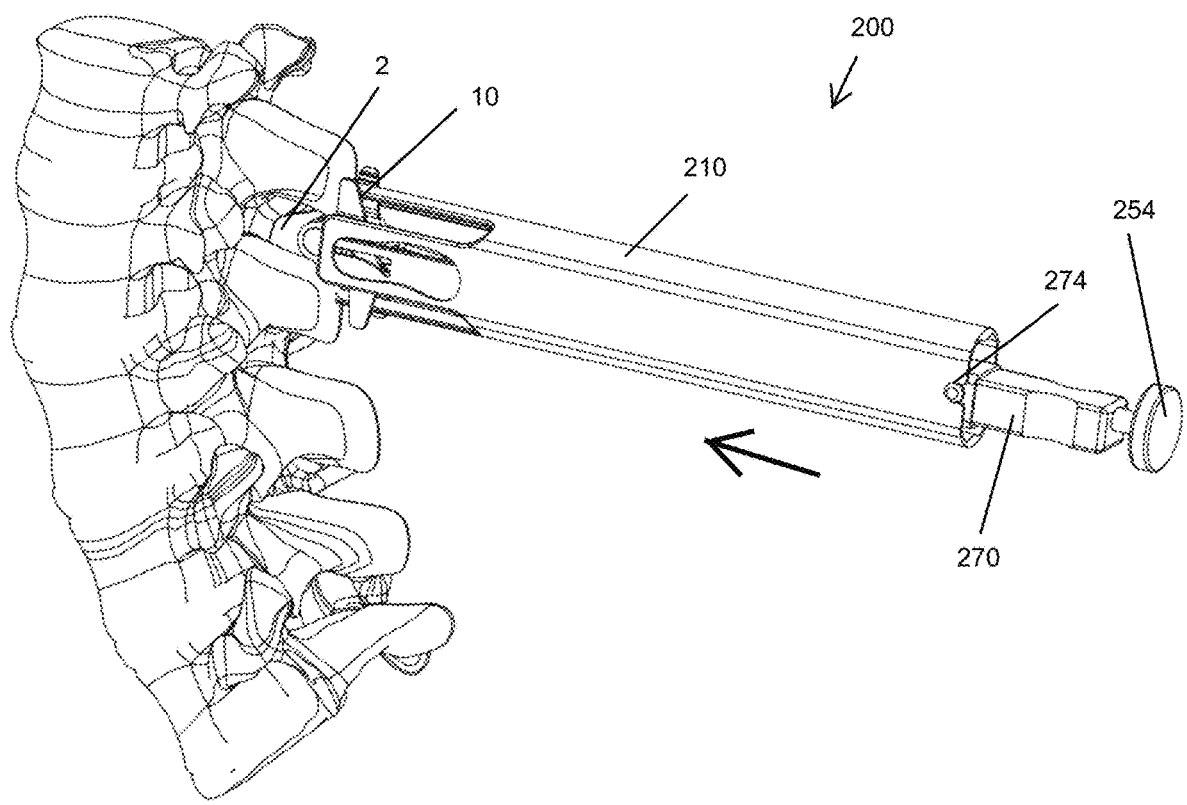
Figure 4F:
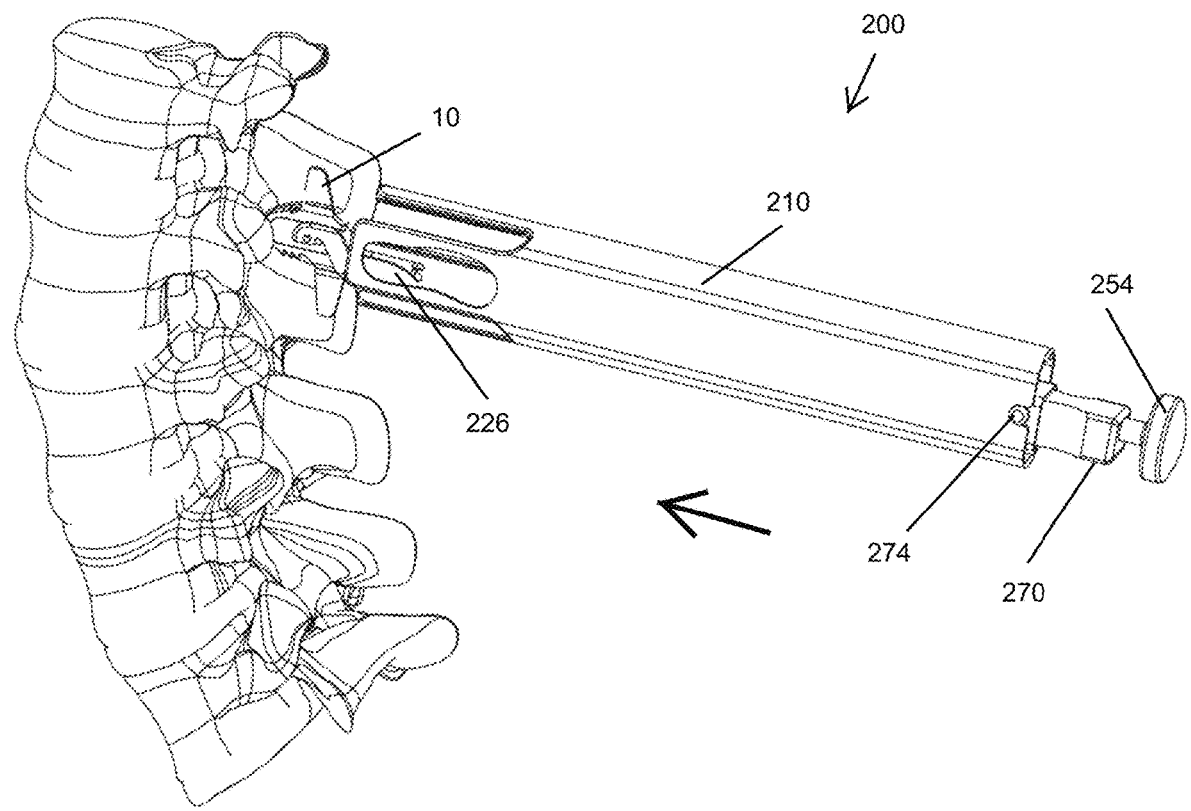
Figure 4G:
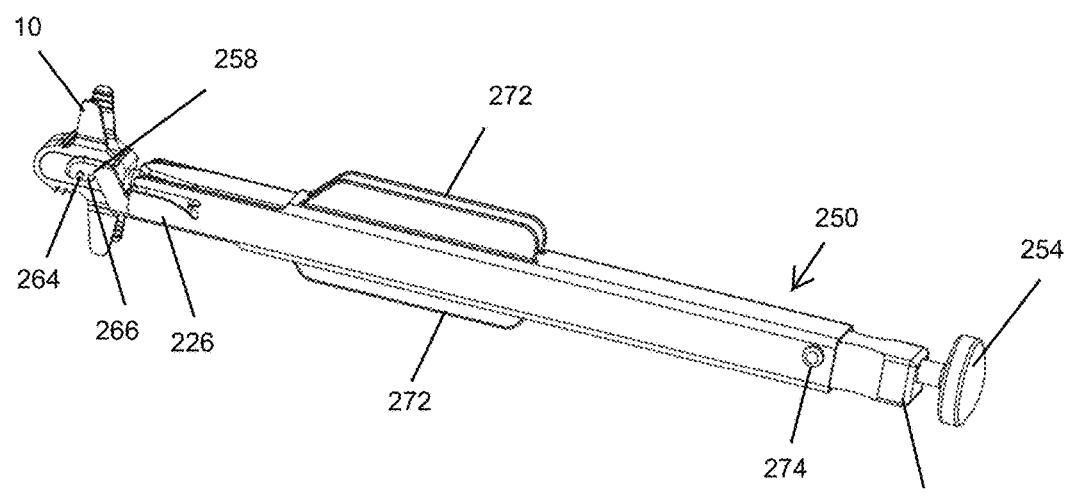

Within shaft 252 of the insertion instrument 250 is another plunging shaft 270 connected to the handle 254. A knob 274 on the proximal end of the shaft 252 serves as a stop and catches onto a notch 228 on the proximal end 214 of the working sleeve 210 of the system 200. As the insertion instrument 250 is placed into the working sleeve 210, the knob 274 catches onto the notch 228 as shown in FIG. 4B. This prevents further advancement of the first shaft 252. Now, the second plunging shaft 270 can be advanced by pushing on the knob 254. This causes the pins 264, 266 to slide against the shoulder 226 portion of the first shaft 252, causing swiveling of the swivel arm 260 of the insertion instrument 250, as shown in FIGS. 4D and 4E. Once the swivel arm 260 has pivoted up to about 90 degrees and the pins 264, 266 are aligned, the second pin 266 can lock against a notch 258 on the bracket of the plunging shaft 270, in a similar manner as described above for the first insertion instrument 150 and as shown in FIG. 4G. This prevents further swiveling and the instrument 250 can now be urged forward through the working sleeve 210 to seat the device 10 properly in between the spinous process and interlaminarly. The insertion instrument 250 can be removed from the working sleeve 210 to leave the device implanted behind.

FIGS. 5A-5G illustrate still another exemplary embodiment of a delivery system 300 in accordance with another aspect of the present disclosure, and methods of using this delivery system 300 to deliver an interspinous, interlaminar device 10 in a minimally invasive manner. Generally speaking, the delivery system 300 is a tubular delivery system through which instruments and devices can pass. Delivery system 300 provides another exemplary embodiment of a working sleeve or delivery tube 310 for implanting an interspinous, interlaminar device 10 in a minimally invasive manner. This delivery tube 310 may be used in combination with the same trocar 230 and insertion instrument 250 of the previously described delivery system 200, as will be described below.

Figure 5A:
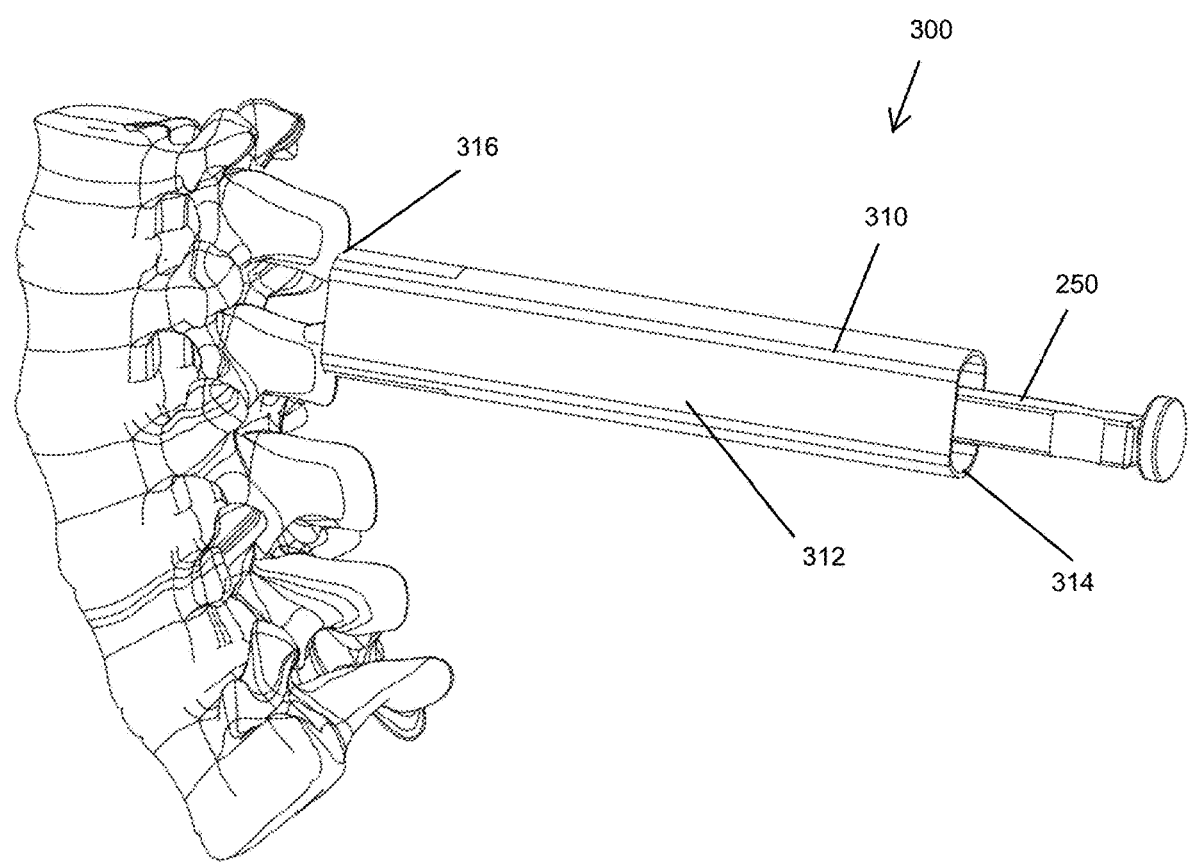
FIGS. 5A-5G illustrate yet another exemplary embodiment of a delivery system of the present disclosure, and method of using the delivery system to implant the interspinous, interlaminar stabilization device of FIG. 1A.
Figure 5B:
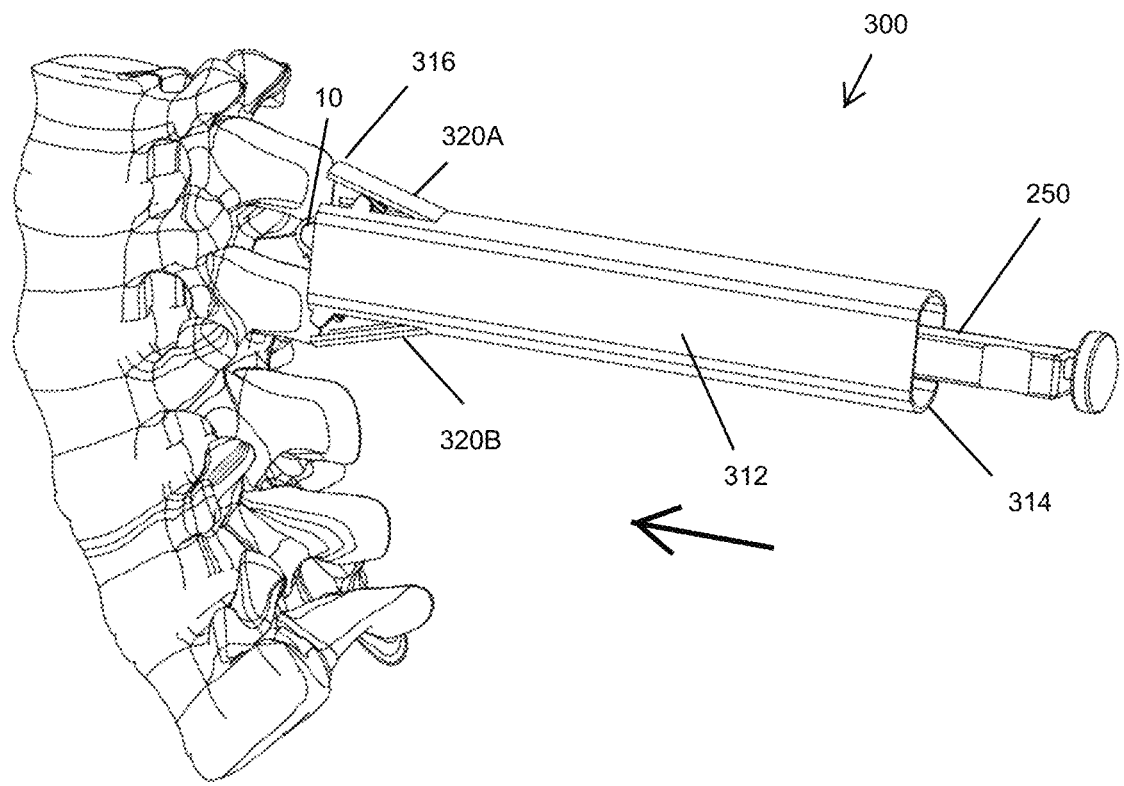
Figure 5C:
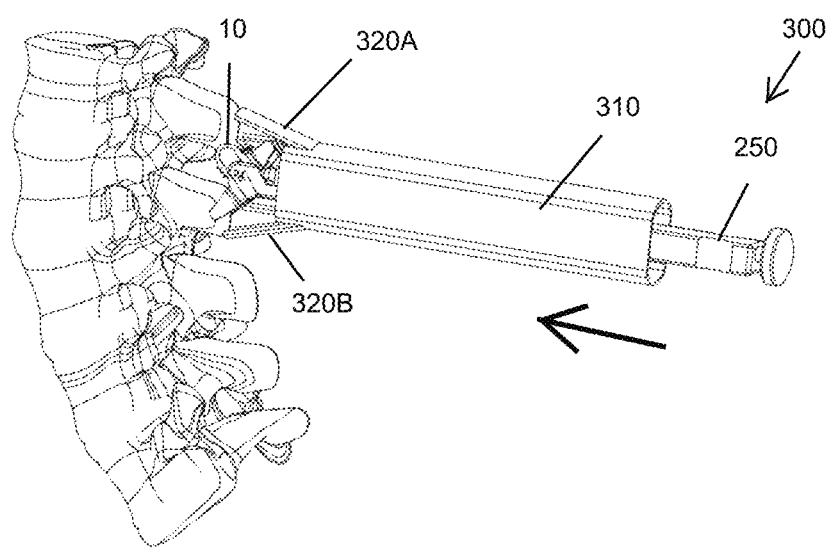
Figure 5D:
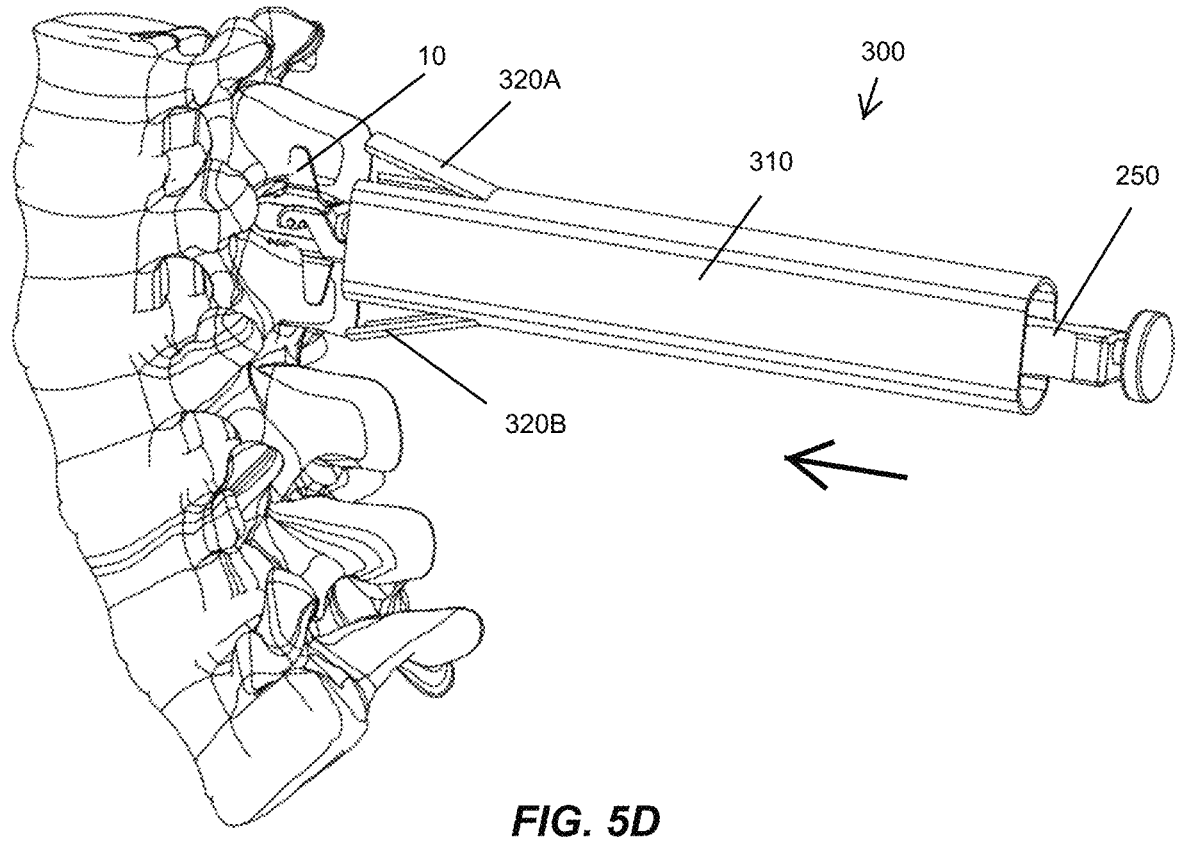
Figure 5E:
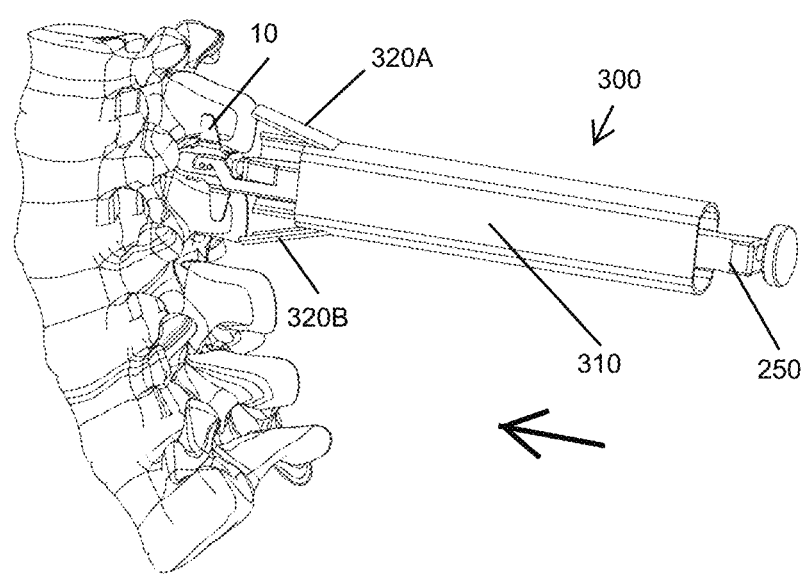
Figure 5F:
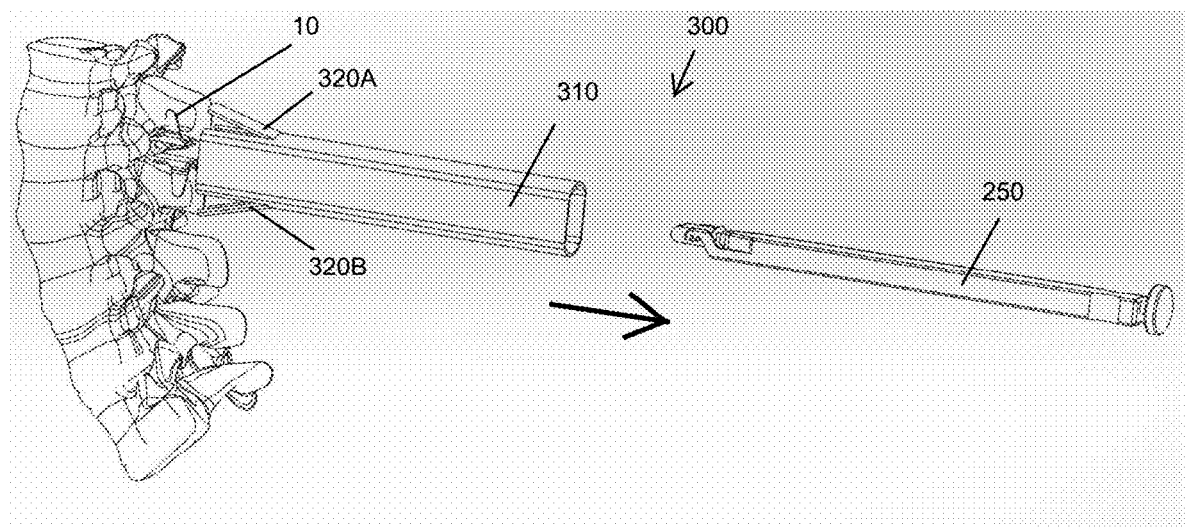
Figure 5G:
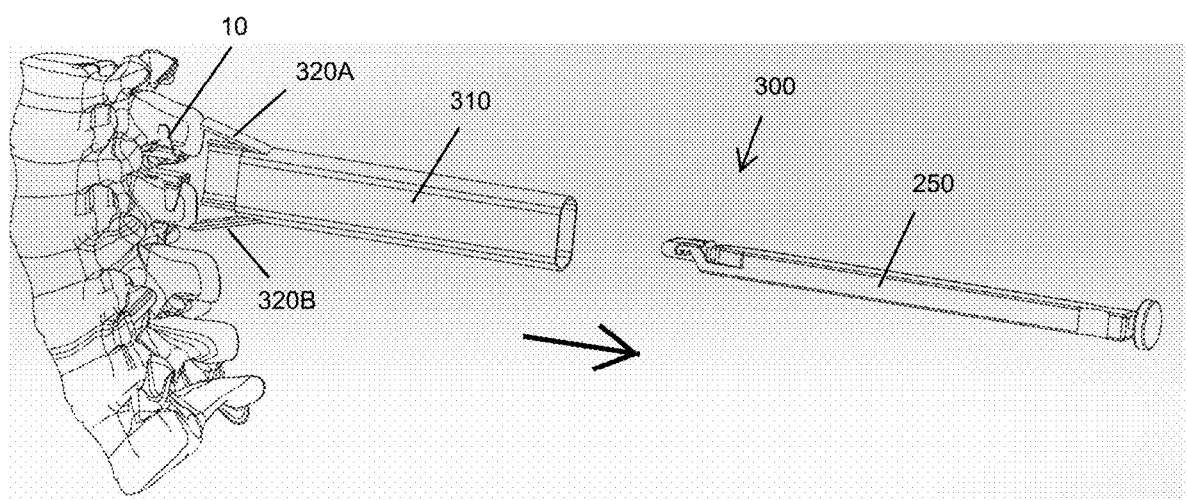

FIG. 5A shows the working sleeve 310 of the present system 300 in use with the insertion instrument 250 of previous system 200. Working sleeve 310 may comprise a hollow tubular body 312 in between a proximal end 314 for insertion of surgical instruments, and a distal end 316 for engaging bone at the insertion site. As shown, the distal end 316 can provide a smooth, continuous surface until the insertion instrument 250 with the attached device 10 is inserted therethrough and swiveled. As shown in FIGS. 5B to 5G, the distal end 316 may include upper and lower flaps or lids 320A, 320B which open to allow the interspinous, interlaminar device 10 to pivot up to about 90 degrees. The clearance from the opened flaps 320A, 320B allows the device 10 to flip to its proper insertion configuration. Advancing the insertion instrument 250 in the manner previously described will cause the device 10 to pivot, urging the device 10 against the flaps 320A, 320B and opening them up. This will allow the user to seat the device 10 properly in between the spinous processes. Then, the insertion instrument 250 can be retracted out of the working sleeve 310 as shown in FIGS. 5F and 5G.

FIGS. 6A-6D illustrate even still another exemplary embodiment of a delivery system 400 in accordance with another aspect of the present disclosure, and methods of using this delivery system 400 to deliver an interspinous, interlaminar device 10 in a minimally invasive manner. Generally speaking, the delivery system 400 is a tubular delivery system through which instruments and devices can pass. Delivery system 400 provides still another exemplary embodiment of a working sleeve or delivery tube 410 for implanting an interspinous, interlaminar device 10 in a minimally invasive manner. This delivery tube 410 may be used in combination with the same trocar 230 and insertion instrument 250 of the previously described delivery system 200, as will be described below.

Figure 6A:
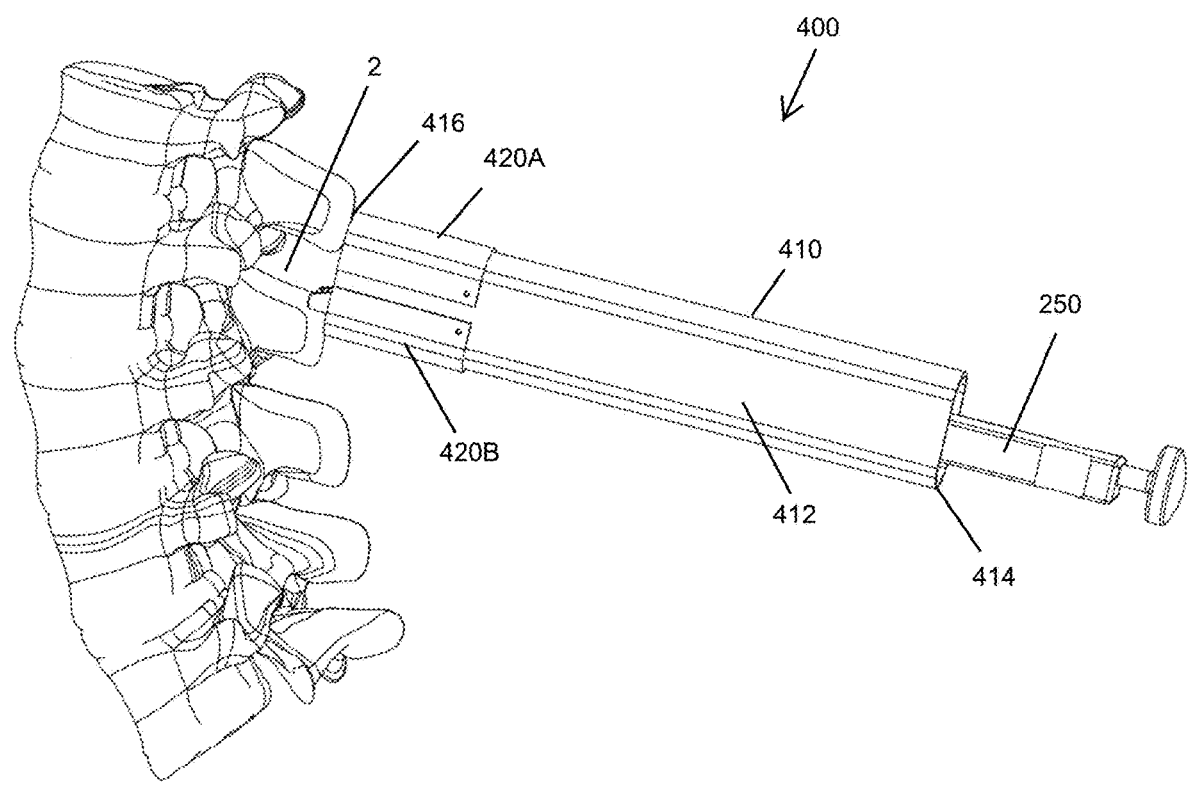
FIGS. 6A-6D illustrate even further still another exemplary embodiment of a delivery system of the present disclosure, and method of using the delivery system to implant the interspinous, interlaminar stabilization device of FIG. 1A.
Figure 6B:
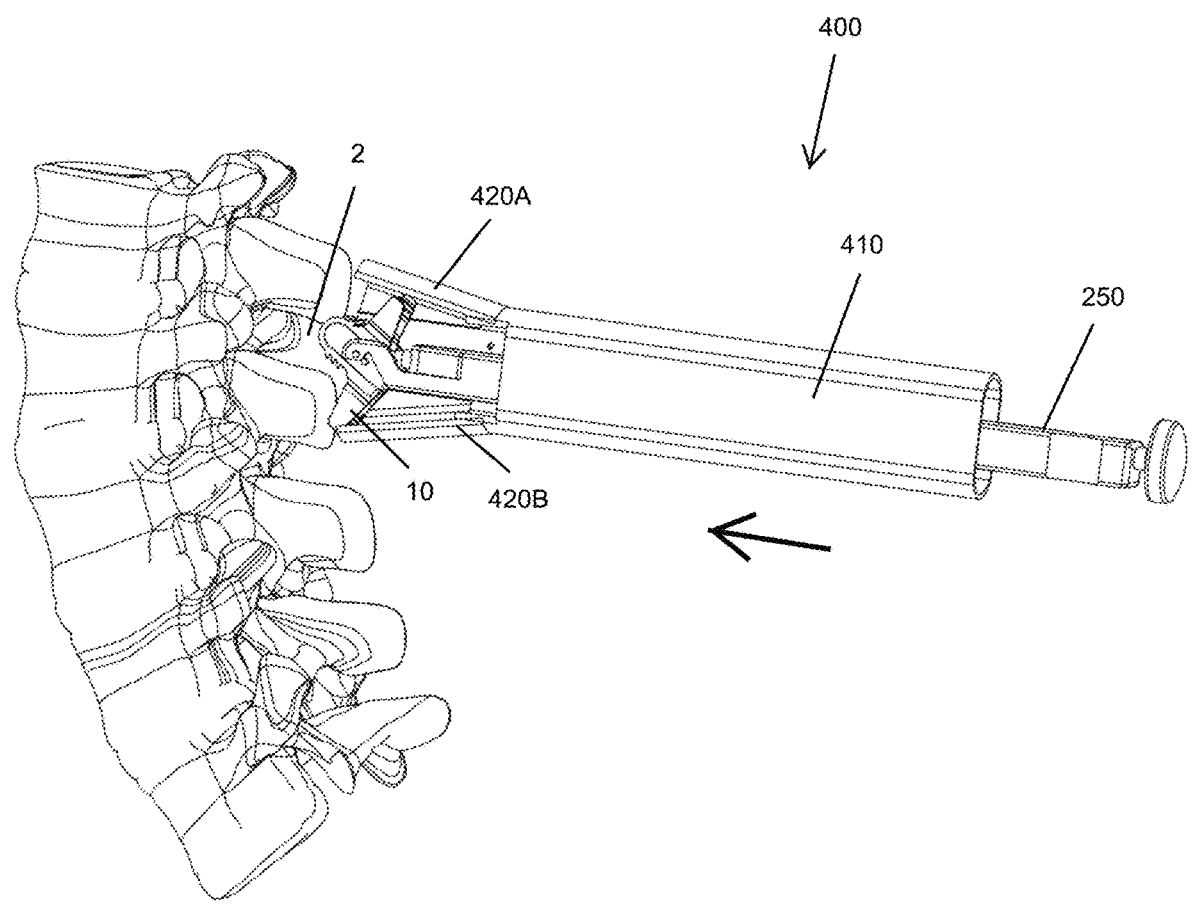
Figure 6C:
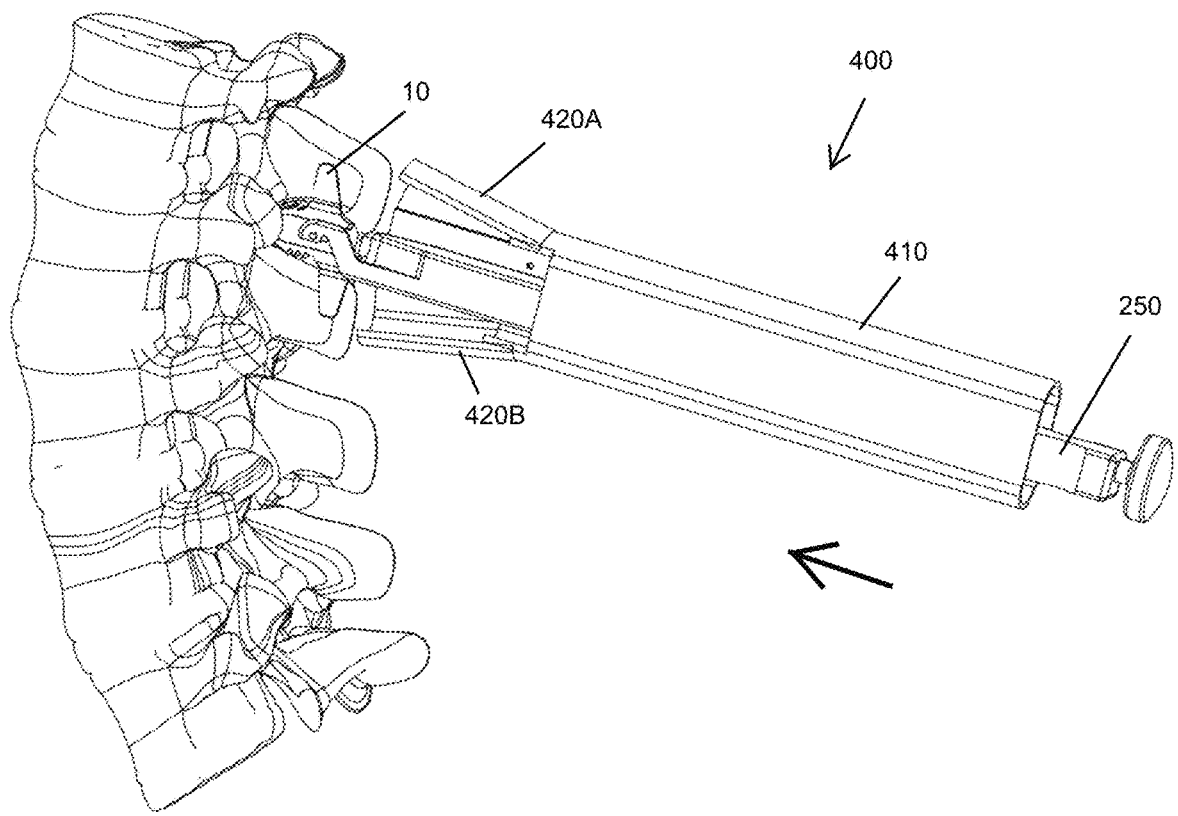
Figure 6D:
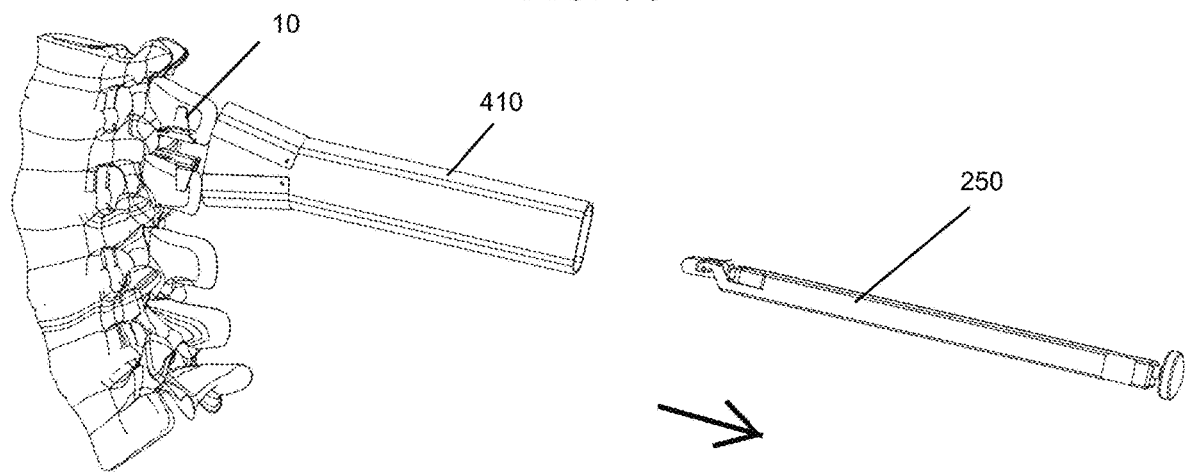

FIG. 6A shows the working sleeve 410 of the present system 400 in use with the insertion instrument 250 of previous system 200. Working sleeve 410 may comprise a hollow tubular body 412 in between a proximal end 414 for insertion of surgical instruments, and a distal end 416 for engaging bone at the insertion site. As shown, the distal end 416 may include hinged upper and lower flaps or lids 420A, 420B which open to allow the interspinous, interlaminar device 10 to pivot up to about 90 degrees. Like working sleeve 310, the clearance from the opened flaps 420A, 420B allows the device 10 to flip to its proper insertion configuration. Advancing the insertion instrument 250 as shown in FIG. 6B will cause the device 10 to pivot, urging the device 10 against the flaps 420A, 420B and opening them up. This will allow the user to seat the device 10 properly in between the spinous processes as shown in FIG. 6C. Then, the insertion instrument 250 can be retracted out of the working sleeve 410 as shown in FIG. 6D.

Figure 7A:
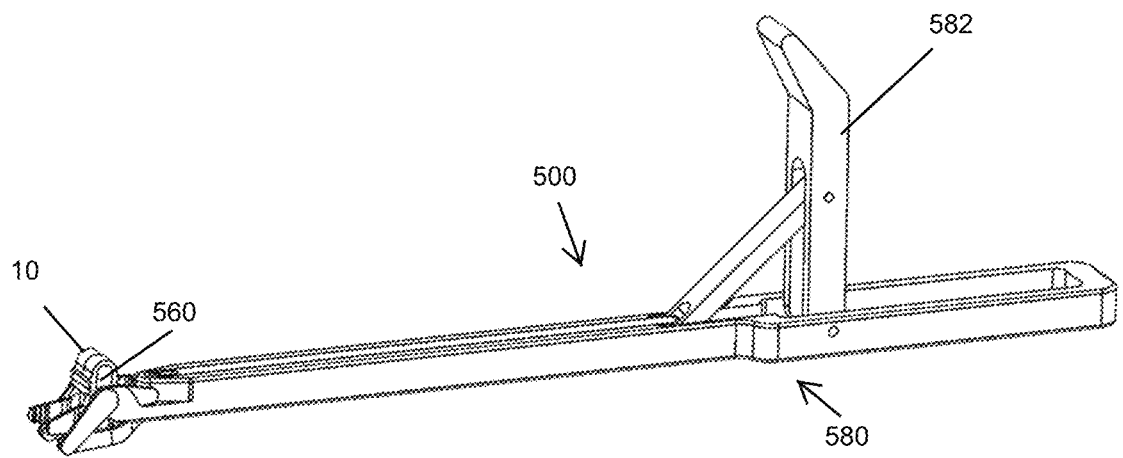
FIGS. 7A-7D illustrate still yet another exemplary embodiment of an insertion instrument of the present disclosure, and method of using the instrument with the interspinous, interlaminar stabilization device of FIG. 1A.
Figure 7B:
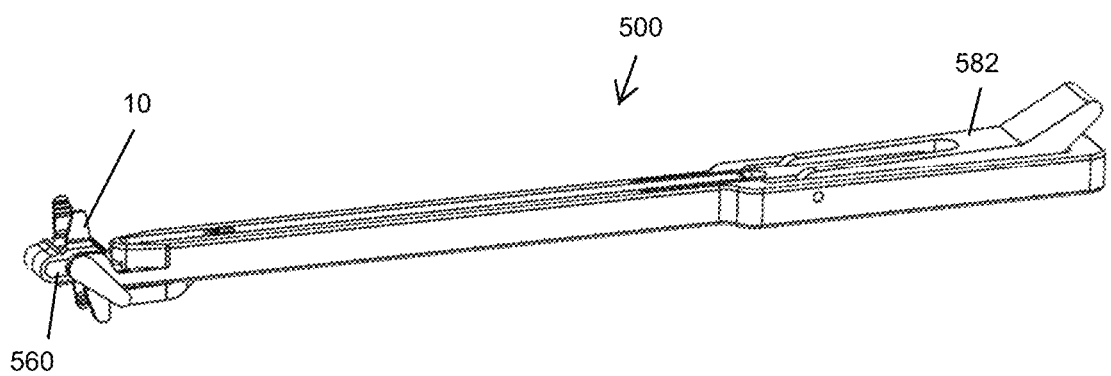
Figure 7C:
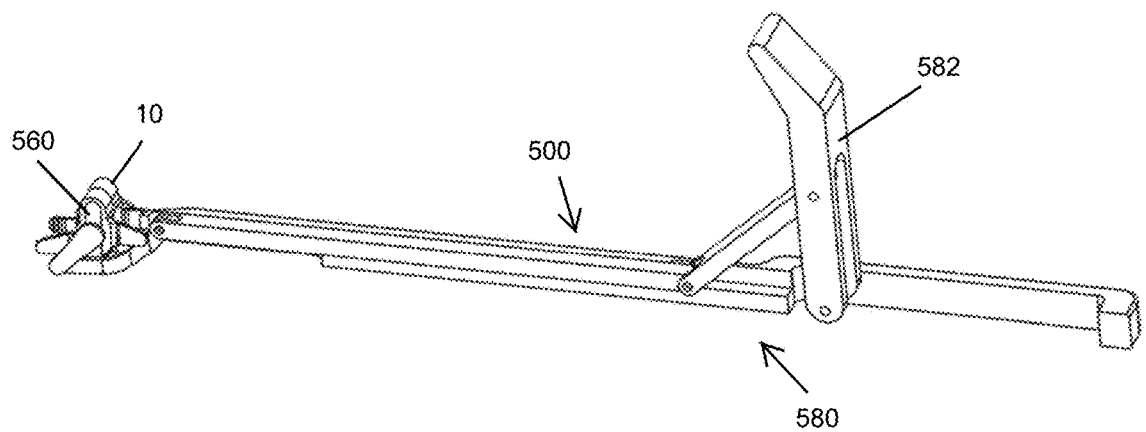
Figure 7D:
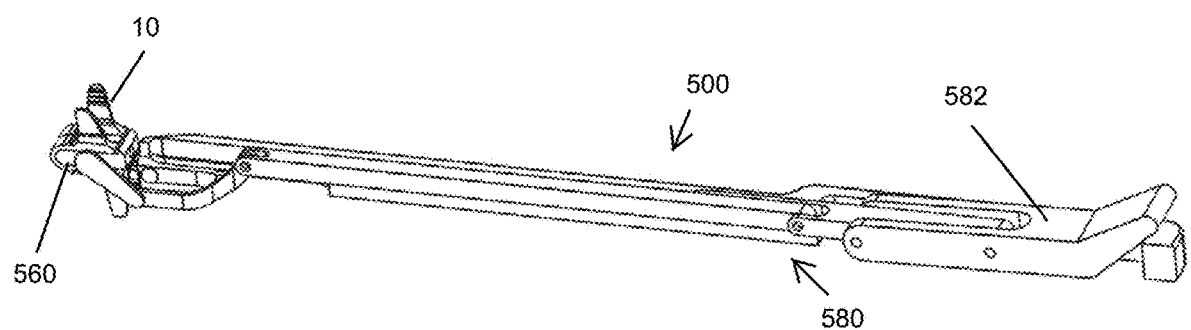

FIGS. 7A-7D illustrate yet another exemplary embodiment of an insertion instrument 500 in accordance with another aspect of the present disclosure, and a method of using this insertion instrument 500. As shown, insertion instrument 500 may comprise a swivel arm 560 for attaching to an interspinous, interlaminar device 10 similar to the previous insertion instrument 150 described above. This swivel arm 560 may be moved by way of a lever arm mechanism 580. As FIG. 7A shows, the attached device 10 resides in a low-profile, lying position with the lever arm 582 of the lever arm mechanism 580 turned up. When the lever arm 582 is lowered as shown in FIG. 7B, the swivel arm 560 is pivoted, causing the device 10 to pivot up to about 90 degrees from a first, low-profile configuration to the second, upright position. This is the proper position for implantation. FIGS. 7C and 7D show partial cutaway views of FIGS. 7A and 7B, respectively, to show the mechanism in action.

Figure 8A:
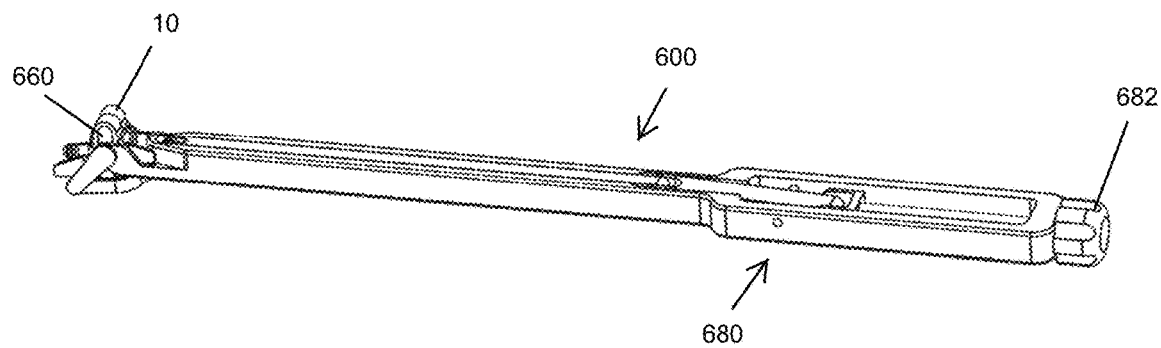
FIGS. 8A-8D illustrate further still another exemplary embodiment of an insertion instrument of the present disclosure, and method of using the instrument with the interspinous, interlaminar stabilization device of FIG. 1A.
Figure 8B:
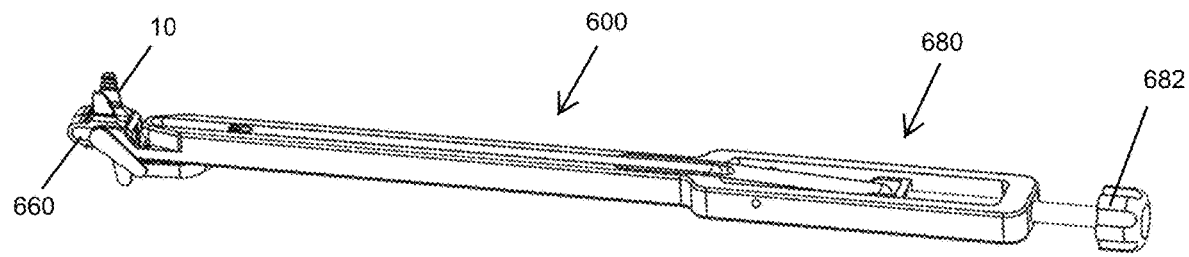
Figure 8C:
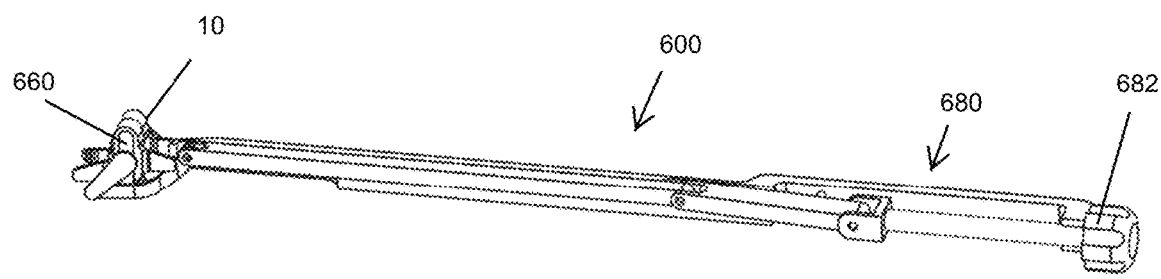
Figure 8D:
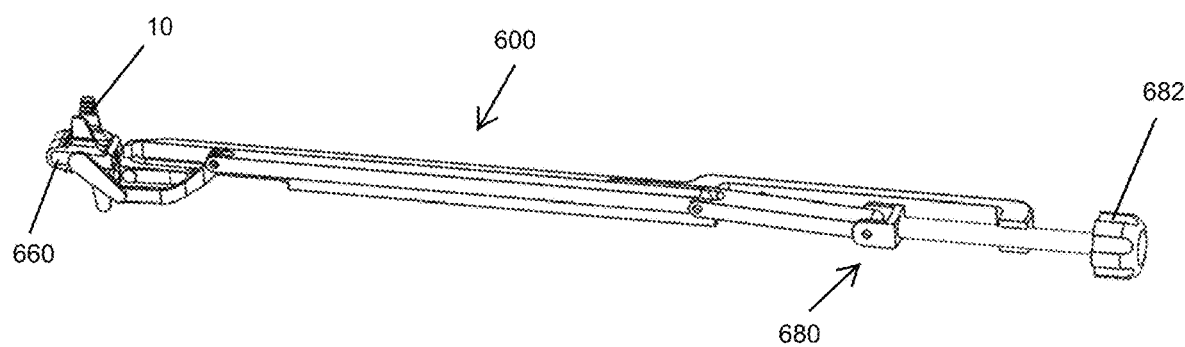

FIGS. 8A-8D illustrate further still another exemplary embodiment of an insertion instrument 600 in accordance with another aspect of the present disclosure, and a method of using this insertion instrument 600. As shown, insertion instrument 600 may comprise a swivel arm 660 for attaching to an interspinous, interlaminar device 10 similar to the previous insertion instrument 150 described above. This swivel arm 660 may be moved by way of a lever/spindle mechanism 680. As FIG. 8A shows, the attached device 10 resides in a low-profile, lying position with the lever/spindle knob 682 of the 680 against the handle 654 instrument 600. When the knob 682 is pulled away as shown in FIG. 8B, the swivel arm 660 is pivoted, causing the device 10 to pivot up to about 90 degrees to the upright position. This is the proper position for implantation. FIGS. 8C and 8D show partial cutaway views of FIGS. 8A and 8B, respectively, to show the mechanism in action.

As mentioned, the surgical instruments and delivery systems provided herein are configured to allow the devices to be delivered in a less invasive manner than is currently performed, and may even be used in a minimally invasive manner. Accordingly, all of the instruments, systems and methods of the present disclosure are capable of use in a minimally invasive surgery (MIS). For example, the surgical instruments and delivery systems may be utilized in an endoscopic procedure.

It should be noted that, while the instruments and method of using the instruments are described above for insertion of an implantable device 10, it is understood that the instruments and methods may also be used with a trial for gauging size and height of the implantation site 2.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A delivery system for delivering a spinal stabilization device to an implantation site external to adjacent vertebrae, the spinal stabilization device having superior and inferior bone-contacting sections and a midsection with a cavity defined therebetween, the spinal stabilization device having a lower profile when the spinal stabilization device is in a first orientation, and having a higher profile when the spinal stabilization device is in a second orientation, the delivery system comprising:

a hollow working sleeve having an instrument insertion end and a bone engagement end, the working sleeve having a profile that is smaller than the higher profile of the spinal stabilization device, the working sleeve further having an inner feature; and an insertion instrument insertable into the instrument insertion end of the working sleeve, the insertion instrument having a movable arm insertable into the defined cavity of the spinal stabilization device and configured to releasably carry the spinal stabilization device through the working sleeve in the first orientation, the movable arm being configured, upon engagement by the inner feature of the working sleeve, to rotate the spinal stabilization device from the first orientation to the second orientation at the implantation site about a rotational axis extending transverse to the superior and inferior bone-contacting sections and through the defined cavity of the spinal stabilization device, wherein the superior and inferior bone-contacting sections extend in a lateral direction relative to an axis defined along a direction of insertion and are intersected by the axis defined along the direction of insertion when the spinal stabilization device is in the first orientation, and wherein the superior and inferior bone-contacting sections extend in a longitudinal direction relative to the axis defined along the direction of insertion when the spinal stabilization device is in the second orientation.

2. The system of claim 1, wherein the spinal stabilization device comprises an interspinous or interlaminar stabilization device.

3. The system of claim 1, wherein the implantation site is between respective adjacent spinous processes of the adjacent vertebrae.

4. The system of claim 1, wherein the distal end of the working sleeve includes a plurality of finger projections.

5. The system of claim 4, wherein the finger projections are expandable.

6. The system of claim 1, wherein the distal end of the working sleeve includes movable flaps.

7. The system of claim 6, wherein the movable flaps are hinged.

8. The system of claim 1, wherein the working sleeve includes guide rails within the hollow elongate body.

9. The system of claim 8, wherein the insertion instrument includes pins for engaging the guide rails of the working sleeve.

10. The system of claim 1, wherein a plurality of lateral walls extend in a lateral direction from at least one section of the superior and inferior bone-contacting sections, wherein the spinal stabilization device rotates between a first, low profile configuration corresponding to the first orientation in which the lateral walls extend in the longitudinal direction and a second, upright configuration corresponding to the second orientation in which the lateral walls extend in the lateral direction, and wherein the second, upright configuration is angled up to about 90 degrees relative to the first, low profile configuration.

11. The system of claim 1, further including a trocar configured for insertion into the working sleeve.

12. The system of claim 3, further including a crimping plier configured for insertion into the working sleeve.

13. The system of claim 12, wherein the crimping plier is configured to crimp the interspinous or interlaminar device onto a spinous process.

14. The system of claim 1, further being configured for endoscopic surgery.

15. The system of claim 1, further being configured for minimally invasive surgery.

16. The delivery system of claim 1, wherein the inner feature of the working sleeve includes a spindle mechanism.

17. The delivery system of claim 1, wherein when the spinal stabilization device is in the second orientation, the movable arm is lockable and the insertion instrument is capable of advancement relative to the working sleeve so as to urge the spinal stabilization device into the implantation site.

18. The delivery system of claim 1, wherein, in the first orientation, the movable arm is positioned such that the superior and inferior bone-contacting sections of the spinal stabilization device extend substantially laterally within the working sleeve.

19. The delivery system of claim 1, wherein, in the second orientation, the movable arm is rotated such that the superior and inferior bone-contacting sections of the spinal stabilization device is pivoted about 90 degrees relative to the first orientation.

* * * * *